(12) United States Patent
Lichtenstein

(10) Patent No.: US 10,654,930 B2
(45) Date of Patent: May 19, 2020

(54) COMPOSITION AND METHOD FOR TREATING AMYOTROPHIC LATERAL SCLEROSIS

(71) Applicant: B. G. NEGEV TECHNOLOGIES AND APPLICATIONS LTD., AT BEN-GURION UNIVERSITY, Be'er Sheba (IL)

(72) Inventor: Rachel Lichtenstein, Omer (IL)

(73) Assignee: B. G. Negev Technologies And Applications Ltd., at Ben-Gurion University, Be'er Sheba (IL)

(*) Notice: Subject to any disclaimer, the term of this patent is extended or adjusted under 35 U.S.C. 154(b) by 0 days.

(21) Appl. No.: 16/079,391

(22) PCT Filed: Feb. 26, 2017

(86) PCT No.: PCT/IL2017/050239
§ 371 (c)(1),
(2) Date: Aug. 23, 2018

(87) PCT Pub. No.: WO2017/145166
PCT Pub. Date: Aug. 31, 2017

(65) Prior Publication Data
US 2019/0048076 A1 Feb. 14, 2019

Related U.S. Application Data
(60) Provisional application No. 62/299,842, filed on Feb. 25, 2016.

(51) Int. Cl.
| *A61P 25/28* | (2006.01) |
| *C07K 16/28* | (2006.01) |
| *C07K 16/00* | (2006.01) |
| C07K 14/705 | (2006.01) |
| A61K 39/00 | (2006.01) |

(52) U.S. Cl.
CPC ........... *C07K 16/283* (2013.01); *A61P 25/28* (2018.01); *C07K 16/00* (2013.01); *A61K 2039/505* (2013.01); *C07K 2317/52* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| 2001/0009898 A1 | 7/2001 | Schubert | |
| 2005/0100965 A1* | 5/2005 | Ghayur | C07K 16/244 435/7.1 |
| 2007/0166306 A1 | 7/2007 | Fey et al. | |
| 2009/0005308 A1 | 1/2009 | Knopf et al. | |
| 2014/0328824 A1* | 11/2014 | Porgador | A61K 38/47 424/94.61 |

FOREIGN PATENT DOCUMENTS

WO 2003011878 A2 2/2003

OTHER PUBLICATIONS

Benatar, M., Lost in translation: Treatment trials in the SOD1 mouse and in human ALS, 2007, Neurobiology of Disease 26:1-13 (Year: 2007).*
DiBernardo et al., Translating preclinical insights into effective human trials in ALS, 2006, Biochimica et Biophysica Acta 1762:1139-1149 (Year: 2006).*
Lichtenstein RG. et al., "Glycans in sera of amyotrophic lateral sclerosis patients and their role in killing neuronal cells", PLOS One, 2012, vol. 7 No. 5, pp. 1-15.
Lichtenstein RG. et al., "Development of stage-dependent glycans on the Fc domains of IgG antibodies of ALS animals", Experimental Neurology, May 2015, vol. 267, pp. 95-106.
George J. Weiner et al., "Anti-CD20 monoclonal antibody with enhanced affinity for CD16 activates NK cells at lower concentrations and more effectively than rituximab", Blood Journal, Oct. 15, 2006, vol. 108 No. 8, pp. 2648-2654.
Anthony RM et al., "Novel roles for the IgG Fc glycan", Annals of the New York Academy of Sciences, Apr. 2012, vol. 1253, pp. 170-180.
International Search Report PCT/IL2017/050239 Completed Jun. 19, 2017; dated Jun. 21, 2017 5 pages.
Written Opinion of the International Searching Authority PCT/IL2017/050239 dated Jun. 21, 2017 7 pages.
Meital Edri-Brami, "In vitro and in vivo Study of the IgG-Fc-glycans and FcγRIIIA Roles in ALS", Theses for Doctor of Philosophy submitted to the Senate of Ben-Gurion University of the Negev, Aug. 13, 2014, 126 pages.
Leitner et al., "Working with ALS Mice, Guidelines for preclinical testing & colony management", Prize4Life & The Jackson Laboratory, Oct. 14, 2009, 28 pages.
Edri-Brami M et al, "Glycans in sera of amyotrophic lateral sclerosis patients and their role in killing neuronal cells", PLOS One, 2012, vol. 7 Issue 5, e35772.

(Continued)

*Primary Examiner* — John D Ulm
(74) *Attorney, Agent, or Firm* — The Roy Gross Law Firm, LLC; Roy Gross

(57) ABSTRACT

The present invention provides a composition and method for treating, delaying the onset, delaying progression of, reducing the incidence of or reducing the severity of amyotrophic lateral sclerosis, in a subject. The composition in some embodiments of the invention is an immunoglobulin derived Fc fragment which binds and partially antagonizes the action of CD16.

8 Claims, 26 Drawing Sheets
Specification includes a Sequence Listing.

(56) References Cited

OTHER PUBLICATIONS

Edri-Brami M et al, "Development of stage-dependent glycans on the Fc domains of IgG antibodies of ALS animals", Experimental Neurology, May 2015, vol. 267, pp. 95-106.
Liu L, "Antibody glycosylation and its impact on the pharmacokinetics and pharmacodynamics of monoclonal antibodies and Fc-fusion proteins", Journal of Pharmaceutical Sciences, Jun. 2015, vol. 104 Issue 6, pp. 1866-1884.
Reusch D, "Fc glycans of therapeutic antibodies as critical quality attributes", Glycobiology, 2015, vol. 25 Issue 12, pp. 1325-1334.
Anthony RM, "Novel roles for the IgG Fc glycan", Annals of the New York Academy of Sciences, Apr. 2012, vol. 1253, pp. 170-180.

* cited by examiner

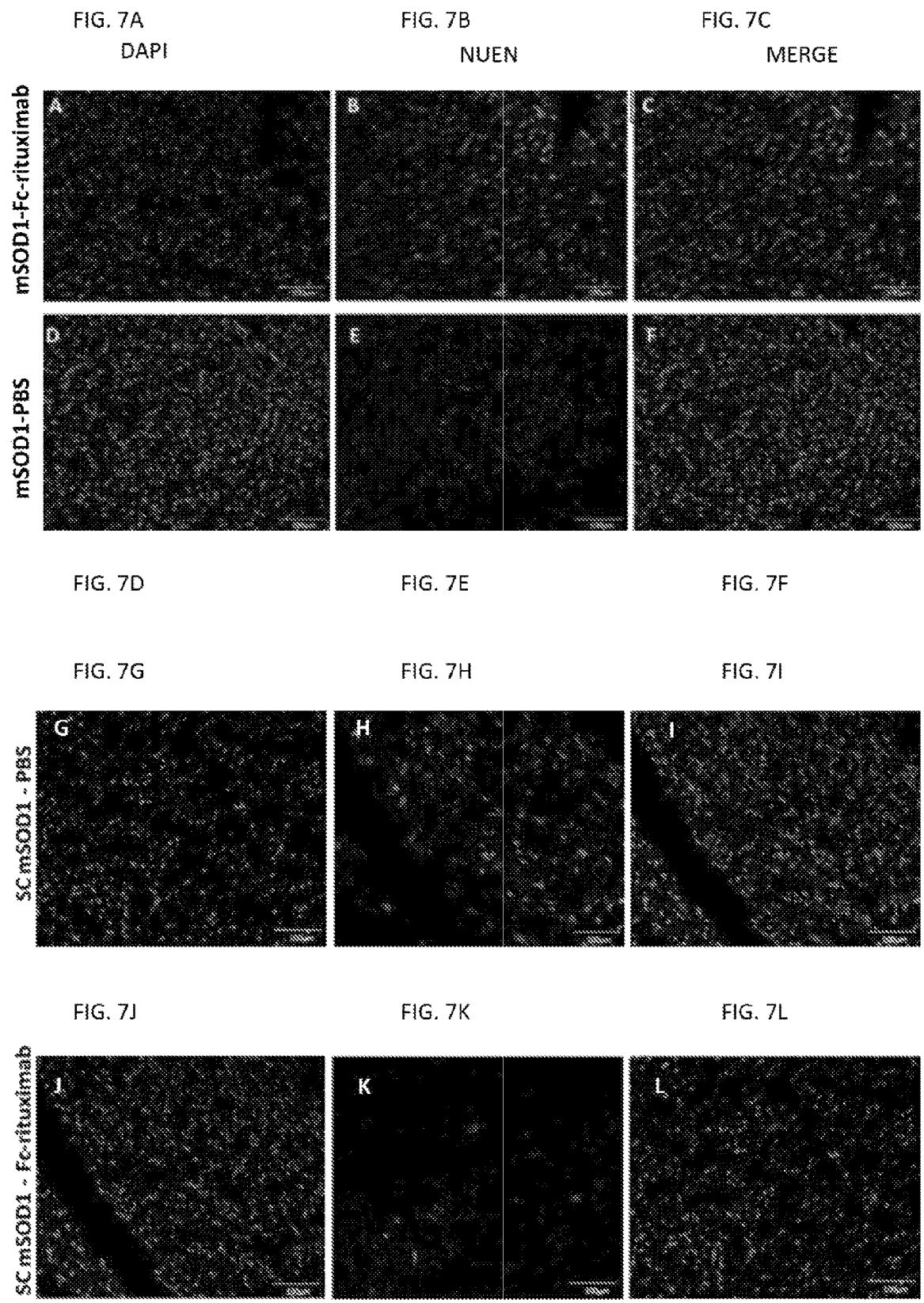
FIGS. 7A-L

SEQUENCE LISTING

```
<160> NUMBER OF SEQ ID NOS: 9

<210> SEQ ID NO 1
<211> LENGTH: 451
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: Xaa is Serine or Alanine
<220> FEATURE:
```

```
<221> NAME/KEY: MISC_FEATURE
<222> LOCATION: (119)..(119)
<223> OTHER INFORMATION: Xaa is Serine or Alanine
<220> FEATURE:
<221> NAME/KEY: MISC_FEATURE
<222> LOCATION: (120)..(120)
<223> OTHER INFORMATION: Xaa is Valine or Alanine
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: MISC_FEATURE
<222> LOCATION: (270)..(270)
<223> OTHER INFORMATION: Xaa is Valanin or Alanine

<400> SEQUENCE: 1

Gln Val Gln Leu Gln Gln Pro Gly Ala Glu Leu Val Lys Pro Gly Ala
 1               5                  10                  15

Ser Val Lys Met Ser Cys Lys Ala Ser Gly Tyr Thr Phe Thr Ser Tyr
             20                  25                  30

Asn Met His Trp Val Lys Gln Thr Pro Gly Arg Gly Leu Glu Trp Ile
         35                  40                  45

Gly Ala Ile Tyr Pro Gly Asn Gly Asp Thr Ser Tyr Asn Gln Lys Phe
     50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
             85                  90                  95

Ala Arg Ser Thr Tyr Tyr Gly Gly Asp Trp Tyr Phe Asn Val Trp Gly
        100                 105                 110

Ala Gly Thr Thr Val Thr Val Xaa Xaa Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Xaa Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 2
<211> LENGTH: 451
<212> TYPE: PRT
<213> ORGANISM: Artificial Sequence
<220> FEATURE:
<223> OTHER INFORMATION: Synthetic

<400> SEQUENCE: 2

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 3
<211> LENGTH: 451
<212> TYPE: PRT
<213> ORGANISM: Artificial Sequence
<220> FEATURE:
<223> OTHER INFORMATION: Synthetic

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ala Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 141
<212> TYPE: PRT
<213> ORGANISM: Artificial Sequence
<220> FEATURE:
<223> OTHER INFORMATION: Synthetic

<400> SEQUENCE: 4

Met Glu Leu Gly Leu Ser Trp Ile Phe Leu Leu Ala Ile Leu Lys Gly
1               5                   10                  15

```
Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
            35                  40                  45

Asn Asp Tyr Ala Met His Trp Val Arg Gln Ala Pro Gly Lys Gly Leu
        50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Gly Met
        115                 120                 125

Asp Val Trp Gly Gln Gly Thr Thr Val Thr Val Ser Ser
        130                 135                 140

<210> SEQ ID NO 5
<211> LENGTH: 141
<212> TYPE: PRT
<213> ORGANISM: Artificial Sequence
<220> FEATURE:
<223> OTHER INFORMATION: Synthetic

<400> SEQUENCE: 5

Met Phe Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
            35                  40                  45

Asn Asp Tyr Ala Met His Trp Val Arg Gln Ala Pro Gly Lys Gly Leu
        50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Gly Met
        115                 120                 125

Asp Val Trp Gly Gln Gly Thr Thr Val Thr Val Ser Ser
        130                 135                 140

<210> SEQ ID NO 6
<211> LENGTH: 120
<212> TYPE: PRT
<213> ORGANISM: Artificial Sequence
<220> FEATURE:
<223> OTHER INFORMATION: Synthetic

<400> SEQUENCE: 6

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Lys Gln Ala Pro Gly Gln Gly Leu Glu Trp Ile
        35                  40                  45
```

Gly Ala Ile Tyr Pro Gly Asn Gly Asp Thr Ser Tyr Asn Gln Lys Phe
            50                  55                  60

Lys Gly Lys Ala Thr Leu Thr Ala Asp Glu Ser Thr Asn Thr Ala Tyr
 65                  70                  75                  80

Met Glu Leu Ser Ser Leu Arg Ser Glu Asp Thr Ala Phe Tyr Tyr Cys
                 85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser
            115                 120

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7

Gln Val Gln Leu Gln Gln Ser Gly Ala Glu Val Lys Lys Pro Gly Ser
 1               5                  10                  15

Ser Val Lys Val Ser Cys Lys Ala Ser Gly Tyr Thr Phe Ser Ser Tyr
                 20                  25                  30

Asn Met His Trp Val Arg Gln Ala Pro Gly Gln Gly Leu Glu Trp Met
             35                  40                  45

Gly Ala Ile Tyr Pro Gly Asn Gly Asp Thr Ser Tyr Asn Gln Lys Phe
            50                  55                  60

Lys Gly Arg Ala Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser
            115                 120

<210> SEQ ID NO 8
<211> LENGTH: 119
<212> TYPE: PRT
<213> ORGANISM: Artificial Sequence
<220> FEATURE:
<223> OTHER INFORMATION: Synthetic

<400> SEQUENCE: 8

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Tyr Ser
                 20                  25                  30

Trp Met Asn Trp Val Arg Gln Ala Pro Gly Gln Gly Leu Glu Trp Met
             35                  40                  45

Gly Arg Ile Phe Pro Gly Asp Gly Asp Thr Asp Tyr Asn Gly Lys Phe
            50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly

```
                      100                 105                 110
Thr Leu Val Thr Val Ser Ser
            115

<210> SEQ ID NO 9
<211> LENGTH: 280
<212> TYPE: PRT
<213> ORGANISM: Artificial Sequence
<220> FEATURE:
<223> OTHER INFORMATION: Synthetic

<400> SEQUENCE: 9

His Thr Phe Pro Ala Val Leu Gln Ser Ser Gly Leu Tyr Ser Leu Ser
1               5                   10                  15

Ser Val Val Thr Val Pro Ser Ser Leu Gly Thr Gln Thr Tyr Ile
            20                  25                  30

Cys Asn Val Asn His Lys Pro Ser Asn Thr Lys Val Asp Lys Lys Val
            35                  40                  45

Glu Pro Lys Ser Cys Asp Lys Thr His Thr Cys Pro Pro Cys Pro Ala
50                  55                  60

Pro Glu Leu Leu Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Lys Phe Asn Trp Tyr Val
                100                 105                 110

Asp Gly Val Glu Val His Asn Ala Lys Thr Lys Pro Arg Glu Glu Gln
            115                 120                 125

Tyr Asn Ser Thr Tyr Arg Val Val Ser Val Leu Thr Val Leu His Gln
    130                 135                 140

Asp Trp Leu Asn Gly Lys Glu Tyr Lys Cys Lys Val Ser Asn Lys Ala
145                 150                 155                 160

Leu Pro Ala Pro Ile Glu Lys Thr Ile Ser Lys Ala Lys Gly Gln Pro
                165                 170                 175

Arg Glu Pro Gln Val Tyr Thr Leu Pro Pro Ser Arg Glu Glu Met Thr
            180                 185                 190

Lys Asn Gln Val Ser Leu Thr Cys Leu Val Lys Gly Phe Tyr Pro Ser
        195                 200                 205

Asp Ile Ala Val Glu Trp Glu Ser Asn Gly Gln Pro Glu Asn Asn Tyr
    210                 215                 220

Lys Thr Thr Pro Pro Val Leu Asp Ser Asp Gly Ser Phe Phe Leu Tyr
225                 230                 235                 240

Ser Lys Leu Thr Val Asp Lys Ser Arg Trp Gln Gln Gly Asn Val Phe
                245                 250                 255

Ser Cys Ser Val Met His Glu Ala Leu His Asn His Tyr Thr Gln Lys
                260                 265                 270

Ser Leu Ser Leu Ser Pro Gly Lys
            275                 280
```

COMPOSITION AND METHOD FOR TREATING AMYOTROPHIC LATERAL SCLEROSIS

CROSS-REFERENCE TO RELATED APPLICATIONS

This application is a National Phase of PCT Patent Application No. PCT/IL2017/050239 having International filing date of Feb. 26, 2017, which claims the benefit of priority of U.S. Provisional Patent Application No. 62/299,842, filed on Feb. 25, 2016, The contents of the above applications are all incorporated by reference as if fully set forth herein in their entirety.

FIELD OF INVENTION

The present invention relates to immunoglobulin derived Fc fragments and their use in treating amyotrophic lateral sclerosis (ALS).

BACKGROUND OF THE INVENTION

Amyotrophic lateral sclerosis (ALS) is the most common progressive neurodegenerative motor neuron disease, causing damage to upper and lower motor neurons, leading to paralysis and death within 3-5 years. Riluzole remains the only effective drug for ALS, but extends the average survival of patients by only 3-6 months. Therefore, discovery of further effective disease-modified therapies is an ultimate aim.

Immunoglobulins of the IgG subtype activate an immune response by simultaneously binding antigens through their variable domains (F(ab)2) and through interaction of their Fc fragment with Fc receptors on immune cells. The human Fc receptor family includes the activating receptor FcγRIIIA (CD 16A) and FcγRIIIB (CD 16B) that mediates immune effector functions.

Analysis of glycosylation patterns of IgG from ALS patients revealed a distinct glycan, A2BG2, in IgG derived from ALS patient's sera. This glycan increases the affinity of IgG to CD 16 on effector cells i.e., microglia (Lichtenstein, et al. PLoS One. 2012; 7(5): e35772.)

Furthermore, the A2BG2 glycan was shown to be specific to ALS. The quantity of A2BG2 increases with disease progression. IgG antibodies identifying extracellular motor neurons are developed at late stages of the disease (Lichtenstein, et al. Exp Neurol. 2015 May; 267:95-106).

Microglial cells are phagocytes of the central nervous system (CNS) possessing similar phenotype as macrophages in the periphery. These cells express CD16 Fc receptors. Inhibition of CD16 mediated microglia activation has been suggested to have therapeutic value for the treatment of ALS, such as in US patent application US 2014\0328824.

Rituximab is a chimeric monoclonal antibody, which encompasses a mouse Fab domain with a CD20 antigenic-binding site and a human Fc fragment with engineered glycans to increase cytotoxicity. This increase was attributed to an increased affinity of the Fc fragment of rituximab to the CD16 Fc receptor (Weiner et. Al., Blood. 2006 Oct. 15; 108(8): 2648-2654).

SUMMARY OF THE INVENTION

In one aspect, the present invention provides a method for treating amyotrophic lateral sclerosis (ALS) in a subject in need thereof, the method comprises administering to said subject a therapeutically effective amount of an immunoglobulin Fc fragment, wherein said Fc fragment comprises a polypeptide comprising the amino acid sequence as set forth in SEQ ID NO: 9 or derivative, a fragment or an analog thereof, thereby treating ALS in said subject.

In another aspect, the present invention provides a pharmaceutical composition comprising an immunoglobulin Fc fragment, and a pharmaceutically acceptable carrier, wherein said Fc fragment comprises a polypeptide comprising the amino acid sequence as set forth in SEQ ID NO: 9 or derivative, a fragment or an analog thereof.

In another embodiment, an Fc fragment of the present invention has an increased affinity to an FC receptor. In another embodiment, said Fc receptor is CD16. In another embodiment, said Fc receptor is expressed on a microglia cell. In another embodiment, an Fc fragment of the present invention is an antagonist of CD16.

In another embodiment, said immunoglobulin Fc fragment comprises two polypeptides, each polypeptide comprising the amino acid sequence as set forth in SEQ ID NO: 9.

In another embodiment, said immunoglobulin Fc fragment comprises N297-glycan. In another embodiment, said immunoglobulin Fc fragment comprises a bisecting N-acetyl glucosamine (GlcNAc).

In another embodiment, the present invention provides a method for enhancing phagocytic activity of microglia in a subject in need thereof, the method comprising administering to said subject the pharmaceutical composition of the present invention, thereby enhancing phagocytic activity of microglia in said subject.

In another embodiment, there is provided the pharmaceutical composition of the present invention for enhancing microglia phagocytosis.

In another embodiment, the present invention provides a method for inhibiting cytotoxicity in a subject in need thereof, comprising administering to said subject the pharmaceutical composition of the present invention, thereby inhibiting cytotoxicity in a subject in need thereof.

In another embodiment, the present invention provides a method for inhibiting antibody-dependent cell-mediated cytotoxicity (ADCC) in a subject in need thereof, comprising administering to said subject the pharmaceutical composition of the present invention, thereby inhibiting ADCC in a subject in need thereof.

In another embodiment, the present invention provides method for inhibiting complement dependent cytotoxicity (CDC) in a subject in need thereof, comprising administering to said subject the pharmaceutical composition of the present invention thereby inhibiting CDC in a subject in need thereof.

Other objects, features and advantages of the present invention will become clear from the following description and drawings.

BRIEF DESCRIPTION OF THE DRAWINGS

FIGS. 7A-7L are representative confocal microscopic images of brain (FIGS. 7A-7F) and SC (FIGS. 7G-7L) taken from 136-day-old mSOD1$^{G93A}$ mice injected with either Fc-rituximab or PBS and immunohistochemically stained with DAPI (blue) and NeuN (green). Scale bar-100 μm.

(FIG. 11B, 11D) and SC (FIG. 11A, 11C) of both mSOD1 and WT mice 7 days after injection of Fc-rituximab or PBS. All samples were normalized to GAPDH housekeeping gene and to mSOD1 mice injected with PBS.

DETAILED DESCRIPTION OF THE INVENTION

Figure 1A:
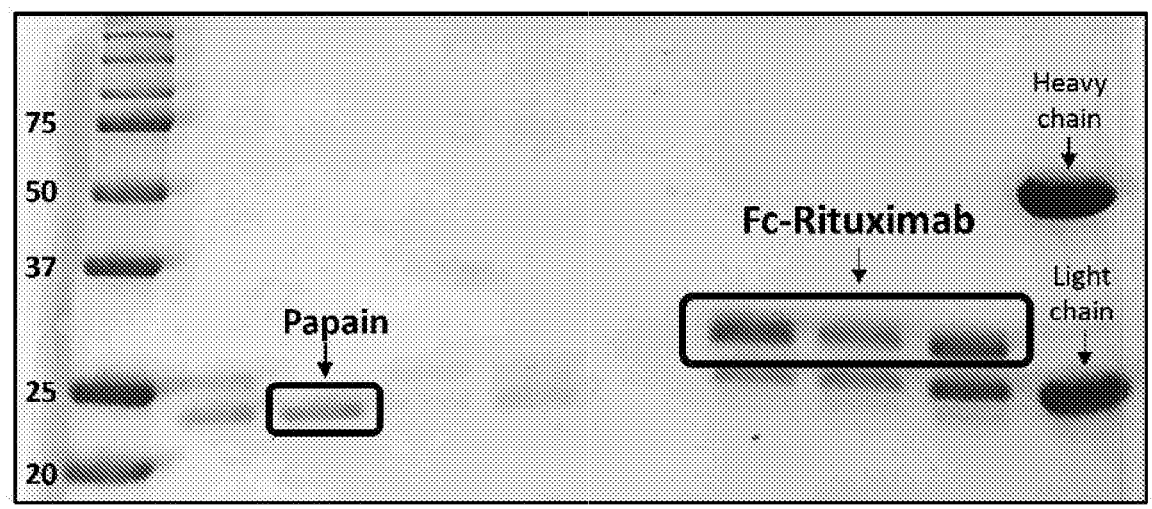
FIG. 1A shows an SDS-PAGE (12%) separation under reducing conditions of: papain, Fc-rituximab of ~30 kDa which results from papain digestion of rituximab following protein G enrichment, and undigested rituximab which having a heavy chain of ~50 kDa and a light chain of 25 kDa.

In one aspect, the present invention provides a method for treating ALS. In some embodiments, the method comprises administering to a subject in need thereof an isolated antibody Fc fragment, wherein said Fc fragment is an antagonist of CD16.

In some embodiments, the CD16 Fc receptor is selected from: FcγRIIIa (CD16a) and FcγRIIIb (CD16b). The Fc fragment of the present invention, in some embodiments, may bind to CD16 on the surface of immune effector cells so as to activate an effector function of an immune effector cell.

The present invention is based, in part, on the surprising finding that administration of the Fc fragment of the invention to a murine model of ALS significantly decreased the ALS progression.

Fc Fragments

The terms "Fc fragment" or "immunoglobulin Fc fragment" as used herein, refer to the C-terminal region of an immunoglobulin. The Fc fragment is a dimeric molecule comprising at least two disulfide-linked antibody heavy chain Fc fragment polypeptides. Fc fragments contains the heavy-chain constant region 2 (CH2) and the heavy-chain constant region (CH3) of an immunoglobulin, and not the variable regions of the heavy and light chains, the heavy-chain constant region 1 (CH1) and the light-chain constant region 1 (CL1) of the immunoglobulin. It may further include the hinge region at the heavy-chain constant region. Also, the immunoglobulin Fc fragment of the present invention may contain a portion or all the heavy-chain constant region 1 (CH1) and/or the light-chain constant region 1 (CL1), except for the variable regions of the heavy and light chains. Also, as long as it has a physiological function substantially similar to or better than the native protein IgG Fc fragment may be a fragment having a deletion in a relatively long portion of the amino acid sequence of CH2 and/or CH3. That is, the immunoglobulin Fc fragment of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region. It should be appreciated to one skilled in the art that the immunoglobulin Fc fragment of the invention are devoid of a Fab region.

In some embodiments, the Fc fragment of the present invention comprises two heavy chain polypeptides linked by at least two disulfide bonds. In another embodiment, the Fc fragment of the present invention comprises two heavy chain polypeptides linked by at between 2 to 4 disulfide bonds. In another embodiment, the Fc fragment of the present invention comprises two heavy chain polypeptides linked by at between 4 to 11 disulfide bonds. In another embodiment, the Fc fragment of the present invention comprises two heavy chain polypeptides linked by at between 11 to 20 disulfide bonds.

As used herein, the term "hinge region" includes the portion of a heavy chain molecule that joins the CHI domain to the CH2 domain. This hinge region comprises approximately 25 residues and is flexible, thus allowing the two N-terminal antigen binding regions to move independently. In another embodiment, the hinge region of the Fc fragment of the present invention has a length of at least 12 amino acids. In another embodiment, the hinge region of the Fc fragment of the present invention has a length of at least 15 amino acids. In another embodiment, the hinge region of the Fc fragment of the present invention has a length of between 12-62 amino acids. In another embodiment, the hinge region of the Fc fragment of the present invention has a length of between 15-62 amino acids.

In some embodiments, Fc fragments may be obtained from native immunoglobulins by isolating whole immunoglobulins from human or animal organisms and treating them with a proteolytic enzyme. Papain digests the native immunoglobulin into Fab and Fc fragments, and pepsin treatment results in the production of pF'c and F (ab') 2 fragments. These fragments may be subjected, for example, to size exclusion chromatography to isolate Fc or pF'c.

In another embodiment, a human-derived Fc fragment is a recombinant immunoglobulin Fc fragment that is obtained from a microorganism.

Fc Glycoform Modification

In another embodiment, the Fc fragment of the present invention may be subjected to glycoform modification. Many polypeptides, including antibodies and Fc fragments, are subjected to a variety of post-translational modifications involving carbohydrate moieties, such as glycosylation with oligosaccharides. There are several factors that can influence glycosylation. The species, tissue and cell type have all been shown to be important in the way that glycosylation occurs. In addition, the immunoglobulin Fc fragment of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method.

In another embodiment, glycoform modification of the Fc fragment of the present invention increases an effector function. In another embodiment, glycoform modification of the Fc fragment of the present invention increases binding affinity to CD16.

The term "glycosylation" means the attachment of oligosaccharides (carbohydrates containing two or more simple sugars linked together e.g. from two to about twelve simple sugars linked together) to the Fc fragment. The oligosaccharide side chains are typically linked to the backbone of the Fc fragment through either N- or O-linkages. In some embodiments, the oligosaccharides of the present invention are attached to a CH2 domain of an Fc fragment as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have at least one site for N-linked glycosylation at amino acid residue 297.

As used herein the term "residue 297" refers to the asparagine at location 297 of an IgG heavy chain, such as Rituximab. In some embodiments, said glycosylation at amino acid residue 297 is of a bisecting-GlcNAc. In some embodiments, said bisecting-GlcNAc lacks a core fucose. In some embodiments, said glycosylation is A2BG2.

In another embodiment, the altered glycosylation comprises an increased level of bisected complex residues in the Fc fragment.

In another embodiment, the altered glycosylation comprises a reduced level of fucose residues in the Fc fragment.

Immunology

In another embodiment, the term "effector cell" as used herein is a cell of the immune system that expresses one or more Fc receptors and mediates one or more effector functions. Effector cells include, but are not limited to, monocytes, macrophages, neutrophils, dendritic cells, eosinophils, mast cells, platelets, B cells, large granular lymphocytes, Langerhans' cells, natural killer (NK) cells, and the central nervous system (CNS) effector cells-microglia.

In another embodiment, the term "effector functions" as used herein refers to those biological activities of an effector cell which are activated by the binding of an Fc fragment to an FC receptor on said effector cell. Examples of effector functions include, but are not limited to, antibody-dependent cellular cytotoxicity (ADCC), antibody-dependent cellular phagocytosis (ADCP), cytokine secretion, immune-complex-mediated antigen uptake by antigen-presenting cells, down-regulation of cell surface receptors, increased Fc-mediated cellular cytotoxicity, increased binding to NK cells, increased binding to macrophages, increased binding to polymorphonuclear cells, increased binding to monocytes, increased direct signaling inducing apoptosis, increased dendritic cell maturation and increased T cell priming.

Antibody-dependent cell-mediated cytotoxicity (ADCC) is a mechanism of cell-mediated immune defense whereby an effector cell of the immune system actively lyses a target cell, whose membrane-surface antigens have been bound by specific antibodies. Activation of ADCC is mediated by binding of the Fc fragment of said specific antibodies to an Fc receptor on the effector cell. Non-limiting examples of Fc receptors are: FcγRIIIA (CD16a), FcγRIIIB (CD16b), FcγRI (CD64), FcγRIIA (CD32), FcγRIIB (CD32), FcaRI (or CD89(, FcεRI and FcεRII (CD23).

In an exemplified embodiment, the Fc fragment of the present invention binds CD16 on a microglia cell.

In another embodiment, the term "antibody dependent cell-mediated phagocytosis" (ADCP) as used herein refers to a cell-mediated reaction wherein nonspecific cytotoxic cells that express Fc receptors recognize bound antibody on a target cell and subsequently cause phagocytosis of the target cell.

The term "target cell" as used herein refers to a cell that expresses a target antigen. The term "target antigen" as used herein is the molecule that is bound specifically by the variable region of a given antibody. A target antigen may be a protein, carbohydrate, lipid, or other chemical compound.

In another embodiment, the Fc fragment of the present invention inhibits, reduces or prevents death of motor neurons by complement dependent cytotoxicity (CDC). The mechanism of CDC is known in the art as the killing of a target cell in which antibody bound to the target cell surface fixes complement which results in assembly of a membrane attack complex that perforates the target cell membrane resulting in subsequent cell lysis. In another embodiment, the Fc fragment of the present invention has an affinity to a complement component e.g., C1q. Binding of the Fc fragment of the present invention to a complement component may inhibit CDC activation and neuronal damage.

In some embodiments, the method of the present invention is used for inhibiting cytotoxicity in the CNS by inhibiting a microglia cell thereby preventing neuronal damage.

The term "cytotoxicity" as used herein refers to the lysis of a target cell by an effector function such as, but not limited to: ADCC and/or CDC.

Fc Variants and Fc Fusions

In another embodiment, the CD16 binding Fc fragment of the present invention is an Fc variant having affinity to CD16.

The term "Fc variant" as used herein refers to an Fc fragment that comprises one or more amino acid modifications relative to a WT Fc fragment, wherein the amino acid modification(s) provide one or more optimized properties. Amino acid modifications include: deletions, insertions, non-conservative or conservative substitutions or combinations thereof of one or more amino acid residues.

In another embodiment, the Fc fragment of the present invention is an Fc variant having at least 90% homology to a WT Fc fragment. In another embodiment, the Fc fragment of the present invention is an Fc Variant having at least 95% homology to a WT Fc fragment. In another embodiment, the Fc fragment of the present invention is an Fc variant having at least 98% homology to a WT Fc fragment. In another embodiment, the Fc fragment of the present invention is an Fc variant having at least 99% homology to a WT Fc fragment.

In some embodiments, the optimized property of the Fc variant of the present invention is an increased affinity to CD16 as compared to WT Fc fragment. By increased affinity it is meant that an Fc variant binds to an CD16 with a significantly higher equilibrium constant of association (Ka) or lower equilibrium constant of dissociation (Kd) than WT Fc Fragment when the amounts of variant and WT Fc fragment in the binding assay are essentially the same. Accordingly, by "reduced affinity" as compared to a WT FC fragment as used herein is meant that an Fc variant binds an Fc receptor with significantly lower Ka or higher Kd than the WT Fc fragment.

In some embodiments, the FC variant of the present invention exhibits an association constant (Ka) of CD16 binding of at least 10 pico molar (pM). In another embodiment, the FC variant of the present invention exhibits an association constant (Ka) of CD16 binding of at least 0.1 nano molar (nM). In another embodiment, the FC variant of the present invention exhibits an association constant (Ka) of CD16 binding of at least 1 nM. In another embodiment, the FC variant of the present invention exhibits an association constant (Ka) of CD16 binding of at least 1 micro molar (μM).

In some embodiments, the optimized property of the Fc variant of the present invention is 2 to 5-fold increased affinity to CD16 as compared to WT Fc fragment. In some embodiments, the optimized property of the Fc variant of the present invention is 5 to 10 fold increased affinity to CD16 as compared to WT Fc fragment. In some embodiments, the optimized property of the Fc variant of the present invention is 10 to 100-fold increased affinity to CD16 as compared to WT Fc fragment. In some embodiments, the optimized property of the Fc variant of the present invention is 100 to 1000-fold increased affinity to CD16 as compared to WT Fc fragment.

In some embodiments, the optimized property of the Fc variant of the present invention is an increased ability to activate ADCC compared to WT Fc fragment as determined by standard assays known in the art. In another embodiment, the Fc variant increases ADCC by at least 10% compared to WT Fc fragment as measured by EC50 values. In another embodiment, the Fc variant increases ADCC by between 10%-50% compared to WT Fc fragment as measured by EC50 values. In another embodiment, the Fc variant increases ADCC by between 50%-100% compared to WT Fc fragment as measured by EC50 values. In another embodiment, the Fc variant increases ADCC by between 100%-500% compared to WT Fc fragment as measured by EC50 values. In another embodiment, the Fc variant increases ADCC by more than 500% compared to WT Fc fragment as measured by EC50 values.

In some embodiments, the optimized property of the Fc variant of the present invention is an increased ability to activate CDC compared to WT Fc fragment as determined by standard assays known in the art. In another embodiment, the Fc variant increases CDC by at least 10% compared to WT Fc fragment as measured by EC50 values. In another embodiment, the Fc variant increases CDC by between 10%-50% compared to WT Fc fragment as measured by EC50 values. In another embodiment, the Fc variant increases CDC by between 50%-100% compared to WT Fc fragment as measured by EC50 values. In another embodiment, the Fc variant increases CDC by between 100%-500% compared to WT Fc fragment as measured by EC50 values. In another embodiment, the Fc variant increases CDC by more than 500% compared to WT Fc fragment as measured by EC50 values.

In some embodiments, the optimized property of the Fc variant of the present invention is a modification to reduce immunogenicity in humans. Modifications to reduce immunogenicity may include modifications that reduce binding of processed peptides derived from the parent sequence to MEW proteins. For example, amino acid modifications may be engineered such that there are no or a minimal number of immune epitopes that are predicted to bind, with high affinity, to any prevalent MEW alleles. Several methods of identifying MEW-binding epitopes in protein sequences are known in the art and may be used to score epitopes in an Fc variant of the present invention.

In another embodiment, the optimized property of the Fc variant of the present invention is an increase in the affinity of the variant Fc fragment for FcγRIIIa (CD16A) and a decrease in the affinity of the variant Fc fragment for FcγRIIIb (CD16B), relative to a comparable molecule comprising a WT Fc fragment which binds FcγRIIIa and FcγRIIIb with WT affinity.

In another embodiment, the optimized property of the Fc variant of the present invention is an increase in the affinity of the variant Fc fragment for FcγRIIIb (CD16B) and a decrease in the affinity of the variant Fc fragment for FcγRIIIa (CD16A), relative to a comparable molecule comprising a WT Fc fragment which binds FcγRIIIa and FcγRIIIb with WT affinity.

In another embodiment, the optimized property of the Fc variant of the present invention is increased or reduced affinity for any Fc receptor. In some embodiments, the Fc variants of the present invention are optimized to possess increased affinity for a human activating Fc receptors, such as, but not limited to, FcγRI, FcγRIIa, FcγRIIc, FcγRIIIa, and FcγRIIIb. In another embodiment, the Fc variants are optimized to possess reduced affinity for the human inhibitory receptor FcγRIIb.

In another embodiment, the alteration of affinity increases an effector function.

In another embodiment, the increase in affinity or effector function is between 2-1000-fold relative to a comparable molecule comprising a WT Fc fragment. In another embodiment, the increase in affinity or effector function is between 2-100-fold relative to a comparable molecule comprising a WT Fc fragment. In another embodiment, the increase in affinity or effector function is between 2-10-fold relative to a comparable molecule comprising a WT Fc fragment. In another embodiment, the increase in affinity or effector function is between 10-100-fold relative to a comparable molecule comprising a WT Fc fragment. In another embodiment, the increase in affinity or effector function is between 100-1000-fold relative to a comparable molecule comprising a WT Fc fragment.

In another embodiment, the Fc variant of the present invention is covalently modified. Covalent modifications of antibodies and antibody fragments are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In another embodiment, the Fc variant of the present invention may be modified by phosphorylation, sulfation, acrylation, glycosylation, methylation, farnesylation, acetylation, amidation, and the like.

In another embodiment, the Fc fragment of the present invention is an Fc fusion. The term "Fc fusion" as used herein is a protein wherein one or more polypeptides is operably linked to an Fc fragment. An Fc fusion combines the Fc fragment of an immunoglobulin with a fusion partner, which in general may be any protein, polypeptide or small molecule. The role of the non-Fc part of an Fc fusion, i.e., the fusion partner, is to mediate target binding, and thus it is functionally analogous to the variable regions of an antibody. Virtually any protein or small molecule may be linked to Fc fragment to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor that is implicated in disease.

In another embodiment, the Fc fragment of the present invention is derived from the antibody registered by ATC code LO1XC02 and known as rituximab or by the commercial names RITUXAN® and MABTHERA®. This antibody is a genetically engineered chimeric human gamma 1 murine constant domain containing monoclonal antibody directed against the human CD20 antigen.

In another embodiment, the Fc fragment of the present invention is isolated using a cysteine protease such as, but not limited to, papain which cleaves Fc from the Fab fragment of rituximab as described in the materials and methods section below.

In another embodiment, the CD16 binding Fc fragment of the present invention is obtained by papain cleavage of an IgG molecule that comprises a polypeptide having a heavy chain with at least 90%, at least 95%, at least 98% identity to the amino acid sequence set forth in SEQ ID NO: 9

(HTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNHYTQKSLSLSPGK)

In another embodiment, the CD16 binding Fc fragment of the present invention is obtained by papain cleavage of an IgG molecule that comprises a polypeptide having a heavy chain with at least 90%, at least 95%, at least 98% identity to the amino acid sequence set forth in SEQ ID NO: 1

(QVQLQQPGAELVKPGASVKMSCKASGYTFTSYNMHWVKQTPGRGLEWIG
AIYPGNGDTSYNQKFKGKATLTADKSSSTAYMQLSSLTSEDSAVYYCARS
TYYGGDWYFNVWGAGTTVTVX₁X₂ASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKKX₃EPKSCDKTHTCPPCPAPELLGGPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLS
LSPGK), wherein X1 is Ser or Ala, X2 is Ser or Ala and X3 is Val or Ala.

In another embodiment, The CD16 binding Fc fragment of the present invention is obtained by papain cleavage of an IgG molecule that comprises a polypeptide having a heavy chain with at least 90%, at least 95%, at least 98% homology to the amino acid sequence set forth in SEQ ID NO: 2

(QVQLQQPGAELVKPGASVKMSCKASGYTFTSYNMHWVKQTPGRGLEWIG
AIYPGNGDTSYNQKFKGKATLTADKSSSTAYMQLSSLTSEDSAVYYCARS
TYYGGDWYFNVWGAGTTVTVSAASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLPPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSP
GK)

In another embodiment, The CD16 binding Fc fragment of the present invention is obtained by papain cleavage of an IgG molecule that comprises a polypeptide having a heavy chain with at least 90%, at least 95%, at least 98% homology to the amino acid sequence set forth in SEQ ID NO: 3

(QVQLQQPGAELVKPGASVKMSCKASGYTFTSYNMHWVKQTPGRGLEWIG
AIYPGNGDTSYNQKFKGKATLTADKSSSTAYMQLSSLTSEDSAVYYCARS
TYYGGDWYFNVWGAGTTVTVASASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKKAEPKSCDKTHTCPPCPAPELLGGPSVFLPPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSP
GK)

In other embodiments, the CD16 binding Fc fragment of the present invention is obtained by papain cleavage of an engineered humanized anti CD20 immunoglobulin.

In another embodiment, the Fc fragment of the present invention is a synthetic peptide generated by methods known in the art.

In general, the synthesis methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha, alpha)-dimethyl-3,5 dimethoxybenzyloxycarbonyl, o-nitrophenylsulfenyl, 2-cyano-t-butyloxycarbonyl, 9-fluorenylmethyloxycarbonyl (FMOC) and the like. In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N, N-dimethylformamide (DMF), and the like. The coupling of successive protected amino acids can be carried out in an automatic polypeptide synthesizer as is well known in the art.

In another embodiment, peptides of the invention may be synthesized such that one or more of the bonds, which link the amino acid residues of the peptides are non-peptide bonds. In another embodiment, the non-peptide bonds include, but are not limited to, imino, ester, hydrazide, semicarbazide, and azo bonds, which can be formed by reactions well known to those skilled in the art.

In one embodiment, the peptides of the present invention, analogs or derivatives thereof produced by recombinant techniques can be purified so that the peptides will be substantially pure when administered to a subject.

As used herein, the term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

In one embodiment, the peptides of the invention are peptide conjugates, comprising the peptides of the present invention derivatives or analogs thereof joined at their amino or carboxyl-terminus or at one of the side chains via a peptide bond to an amino acid sequence of a different protein. In another embodiment, conjugates comprising peptides of the invention and a different protein can be made by protein synthesis. In another embodiment, conjugates comprising peptides of the invention and a different protein can be made by use of a peptide synthesizer. In another embodiment, conjugates comprising peptides of the invention and a different protein can be made by ligating the appropriate nucleic acid sequences encoding the desired amino acid sequences to each other by methods known in the art, in the proper coding frame, and expressing the conjugate by methods commonly known in the art. In another embodiment, addition of amino acid residues may be performed at either terminus of the peptides of the invention for the purpose of providing a "linker" by which the peptides of this invention can be conveniently bound to a carrier. In another embodiment, the linkers are comprised of at least one amino acid residue. In another embodiment, the linkers can be of 40 or more residues. In another embodiment, the linkers are comprised of 1 to 10 residues. In another embodiment, amino acid residues used for linking are tyrosine, cysteine, lysine, glutamic and aspartic acid, or the like.

In another embodiment, the Fc fragment of the present invention is obtained by protease cleavage of an IgG isotype immunoglobulin. The group of IgG immunoglobulins includes the isotypes: IgG1, IgG2, IgG3 and IgG4.

The term "wild-type (WT) Fc fragment" as used herein refers to an Fc fragment having the amino acid sequence identical to the amino acid sequence of an Fc fragment obtained by protease cleavage of a WT immunoglobulin found in nature.

In another embodiment, a WT immunoglobulin of the present invention is a native human IgG1. Non-limiting examples of WT IgG1 comprise the amino acid sequences set forth in gene accession numbers: J00228, Z17370 and Y14737, IgG2, including J00230, AJ250170, AF449616, AF449617, AF449618, Z49802 and Z49801, IgG3 including M12958, K01313, X16110, X99549, AJ390236, AJ390237, AJ390238, AJ390241, AJ390242, AJ390246, AJ390247, AJ390252, AJ390244, AJ390254, AJ390260, AJ390262, AJ390272, AJ390276 and AJ390279.

In another embodiment, a WT immunoglobulin of the present invention is a native human IgG2. Non-limiting examples of WT IgG2 comprise the amino acid sequences set forth in gene accession numbers: J00230, AL928742, AJ250170 and AF449617.

In another embodiment, a WT immunoglobulin of the present invention is a native human IgG3. Non-limiting examples of WT IgG3 comprise the amino acid sequences set forth in gene accession numbers: AJ390236, X995549, AJ390247, AJ390252, AJ380237, AJ390241, AJ390244, X16110, AJ390254, AJ390263, AJ390272, AJ390276, and AJ390279.

In another embodiment, a WT immunoglobulin of the present invention is a native human IgG4. Non-limiting examples of WT IgG4 comprise the amino acid sequences set forth in gene accession numbers: K01316, AJ001564 and AJ001563.

In another embodiment, Fc fragments of the present invention may be obtained from native forms isolated from humans and other animals including cows, goats, swine, mice, rabbits, hamsters, rats and guinea pigs, or may be recombinants or derivatives thereof, obtained from transformed animal cells or microorganisms.

In another embodiment, the CD16 binding Fc fragment of the present invention is obtained by papain cleavage of ofatumumab. The amino acid sequence of the heavy chain of ofatumumab is set forth in SEQ ID NO: 04 and SEQ IS NO: 05.

In another embodiment, the CD16 binding Fc fragment of the present invention is obtained by papain cleavage of veltuzumab. The amino acid sequence of the heavy chain of veltuzumab is set forth in SEQ ID NO: 06 and SEQ ID NO: 07.

In another embodiment, the CD16 binding Fc fragment of the present invention is obtained by papain cleavage of a humanized type II anti-CD20 IgG1 antibody with bisected a fucosylated carbohydrates in its Fc region. The amino acid sequence of the heavy chain the humanized type II anti-CD20 IgG1 antibody with bisected a fucosylated carbohydrates in its Fc region is set forth in SEQ ID NO: 08.

Other non-limiting examples of engineered humanized anti CD20 immunoglobulins include, but are not limited to: ocrelizumab, obinutuzumab, Belimumab and atacicept.

Therapeutic Methods

In one aspect, the present invention provides a method of treating, delaying the onset, delaying progression of, reducing the incidence of or reducing the severity of ALS in a subject, said method comprising administering to a subject antibody derived Fc fragments or derivative thereof, wherein said Fc fragments or derivative thereof has increased binding specificity to an Fc receptor on an effector cell, thereby treating a subject afflicted with ALS.

In some embodiments, the term "treatment" as used herein refers to any response to, or anticipation of ALS and includes but is not limited to: preventing the ALS from occurring in a subject, which may or may not be predisposed to the condition, but has not yet been diagnosed with ALS and accordingly, the treatment constitutes prophylactic treatment for ALS; inhibiting ALS, e.g., arresting, slowing or delaying the onset, development or progression of the ALS; or relieving ALS, e.g., causing regression of the ALS or reducing the symptoms of ALS.

ALS is a fatal neurodegenerative disease caused by degeneration of the upper and lower motor neurons. ALS patients and animal models of inherited ALS, like mutant Cu/Zn superoxide dismutase (mSOD1), display similar inflammatory responses at the site of the motor neuron injury, enabling both the CNS resident and systemic inflammatory cells to balance between neuroprotection and neurotoxicity. One population involved in these inflammatory responses is microglia cells, which during their activation change morphology, surface receptor expression, and produce growth factors and cytokines, leading to neuron protection or injury depending on the physiological conditions. The manners in which the signals switch between protective to cytotoxic microglia are not yet fully understood. However, ALS progression is attributed, in part, to cytotoxic microglia cells, which activate antibody-dependent cell-mediated cytotoxicity (ADCC) leading to neuron damage.

In another embodiment, administering the Fc fragment of the present invention to a subject afflicted with ALS prevents microglia mediated cytotoxicity by ADCC of a target cell thereby preventing neuronal damage, thus treating the subject.

In another embodiment, the term "administering" as used herein, includes delivery of effective amounts of the composition of the present invention to a subject in need thereof. Methods for delivery of antibodies and antibody fragments are well known in the art.

In order to treat a patient, a therapeutically effective dose of the Fc fragment of the present invention is administered. By "therapeutically effective dose" herein is meant a dose that produces the effects for which it is administered. The exact dose will depend on the purpose of the treatment, and will be ascertainable by one skilled in the art using known techniques. In some embodiments, dosages may range from 0.01 to 1000 mg/kg of subject body weight per day. In some embodiments, dosages may range from 0.1 to 50 mg/kg of subject body weight per day. In some embodiments, dosages may range from 1 to 100 mg/kg of subject body weight per day. In some embodiments, dosages may range from 1 to 500 mg/kg of subject body weight per day. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

In some embodiments, there is provided pharmaceutical compositions comprising as an active ingredient a therapeutically effective amount of the Fc fragment present invention, and a pharmaceutically acceptable carrier or diluents.

The term "carrier" refers to a diluent, adjuvant, excipient, or vehicle with which the Fc fragment is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the peptide of the invention, preferably in a substantially purified form, together with a suitable amount of carrier so as to provide the form for proper administration to the subject.

In another embodiment, administration of the pharmaceutical composition comprising the Fc fragment of the present invention, preferably in the form of a sterile aqueous solution, may be done in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance® pulmonary delivery system commercially available from Inhale Therapeutics), vaginally, parenterally, rectally, or intraocularly. Moreover, one may administer one or more initial dose(s) of the Fc fragment followed by one or more subsequent dose(s), wherein the mg/kg of subject body weight per day dose of the Fc fragment c in the subsequent dose(s) exceeds the mg/kg of subject body weight per day dose of the Fc fragment in the initial dose(s). For example, the initial dose may be in the range from about 20 mg/kg of subject body weight per day to about 250 mg/kg of subject body weight per day (e.g., from about 50 mg/kg of subject body weight per day to about 200 mg/kg of subject body weight per day) and the subsequent dose may be in the range from about 250 mg/kg of subject body weight per day to about 1000 mg/kg of subject body weight per day.

In another embodiment, the Fc fragment of the present invention is the only therapeutically active agent administered to a patient. Alternatively, the Fc fragment is administered in combination with one or more other therapeutic agents affective for the treatment of ALS, including but not limited to Riluzole. The Fc fragment may be administered concomitantly with one or more antibodies, which may or may not comprise an Fc variant of the present invention.

In some embodiments, the Fc fragment of the present invention is an antagonist of CD16. The term "antagonist" is used in its normal sense in the art i.e., a chemical compound which prevents functional activation of a receptor (CD16, in this case) by its agonist.

The term "agonist" is known in the art as a chemical that binds to a receptor and activates the receptor to produce a biological response.

In some embodiments, the Fc fragment of the present invention is a partial antagonist of a CD16 Fc receptor. The term "partial antagonist" as used herein is an Fc fragment which is capable of specifically binding an Fc receptor wherein said binding elicits some effector functions but does not elicit other effector functions that are normally elicited by binding of an Fc of an IgG to the CD16 Fc receptor.

In some embodiments, the Fc fragment of the present invention agonizes at least one effector function of an Fc receptor, or antagonizes at least one effector function of an Fc receptor.

In some embodiments, binding of the Fc fragment of the present invention to an Fc receptor on an effector cells elicits cytokine secretion i.e., IL-2 but blocks cytotoxicity i.e., by ADCC thereby preventing neuronal damage.

In some embodiments, administering the CD16 binding Fc fragment to a subject afflicted with ALS prevents or reduces weight loss of said subject.

In some embodiments, administering the CD16 binding Fc fragment to a subject afflicted with ALS prevents or reduces the extent of damage to lower and/or upper motor neurons as measured by methods known in the art.

In some embodiments, administering the CD16 binding Fc fragment to a subject afflicted with ALS prevents or decelerates disease progression as measured by neurological score (see example 2).

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods

Rituximab Injection Protocol

Male and female mSOD1$^{G93A}$ mice and their age-matched littermates at 70 days of age were administered Fc rituximab or PBS as control via intrathecal injections. The BBB penetrability was increased 20 min prior to intrathecal injection; mice were weighed then Mannitol (20%: in the ratio of 1/20 (Mannitol volume (μL)/mouse weight (gr)); Baxter Healthcare Corporation) were injected intra-peritoneum (IP). 10 min later mice were anesthetized using 100 μL intra-muscular (IM) injection of Ketamin and Xylazine mixture (200 μL of Ketamin with 100 μL of Xylazine diluted up to 4 mL with PBS). After 10 min, when mice dazed, 100 μL of diluted Fc-rituximab (5 μg/mL in PBS) were intrathecal injected into the cerebrospinal fluid ventricle, using 40° folded 23G needles. After injection, mice were weighed and evaluated by neurological disability. Neurological score of four limbs was blindly performed by an independent physiotherapist using the scale of 0-5, with 0 being normal and 5 being completely paralyzed as suggesting in preclinical testing guidelines for ALS mice (Leithner et al., 2009).

Brain and Spinal Cord Extraction

Brains and spinal cords were extracted from a mice transcardially perfused with PBS. Tissues were fixed with 4% formaldehyde and cryoprotected in 30% sucrose solution. Finally, samples were frozen in OCT and cut into 18 μm sections for immunofluorescence.

In Vivo Imaging

In vivo imaging studies were conducted using the IVIS® Lumina LT Series III preclinical in vivo imaging system.

In TNF-α ELISA assay—Brains and spinal cord were obtained from treated and untreated mice, and TNF-α was quantified with TNF-α ELISA kit (Biolegened) according to the manufacturer's instruction.

Gene Expression

Total RNA was isolated by the EZ-RNA kit (Biological Industries) according to the manufacturer's instruction RNA was reverse transcribed into cDNA using the high capacity cDNA reverse transcription kit (Applied Biosystems) and cDNA was used for quantitative real-time PCR (qRT-PCR) analysis.

Digestion of Rituximab (IgGs) and Enrichment of the Fc's Fragment

Rituximab Fc's fragments were prepared by papain digestion and enriched by protein G. Volume of 10 μL rituximab (10 mg/ml; Roche) was treated with 15 μL of papain (0.5 mg/ml; Sigma) in the presence of 75 μL cysteine solution (5 mM; Sigma) for 1 hr at 37° C. The reaction was stopped by adding 100 μL of iodoacetamide (5 mg/ml; Sigma). According to the manufacturer's instructions (GE healthcare, Germany) the Fc fragments were separated from the Fab fragments using protein G sepharose. Briefly, 1 volume of digested rituximab (100 μL) diluted with 1 volume of binding buffer (20 mM sodium phosphate, pH 7.0) was applied onto a protein G column. After 1 h of incubation at room temperature under rotating conditions, the beads were washed, the Fc bounded fraction was eluted with 100 μL of elution buffer (0.1 M glycine-HCl, pH 2.7), and the supernatants were collected into 1 M Tris-HCl, pH 8.5, to neutralize the Fc solutions to pH 7.5. Fc concentration was determined by Bradford assay (Bio-Rad, Hercules, Calif.). The Fc samples were immediately frozen for storage at −20° C. until thawed for injection or in vitro activity and inhibition assays.

Example 1

Rituximab-Derived Fc Fragment Binds CD16 and Acts as a Partial CD16 Antagonist

A natural Fc fragment has been isolated using cysteine protease (papain) that cleaves Fc from the Fab fragment of the commercial drug rituximab. In order to characterize the size of the FC fragment, rituximab was subjected to papain digestion followed by protein G enrichment and the resulting fragment (FC-Rituximab) as well as the undigested Rituximab (intact Rituximab) were subjected to gel electrophoresis using SDS-PAGE (12%), under reducing conditions. Subsequently, the gel was stained using Coomassie Brilliant Blue staining (FIG. 1A).

Figure 1B:
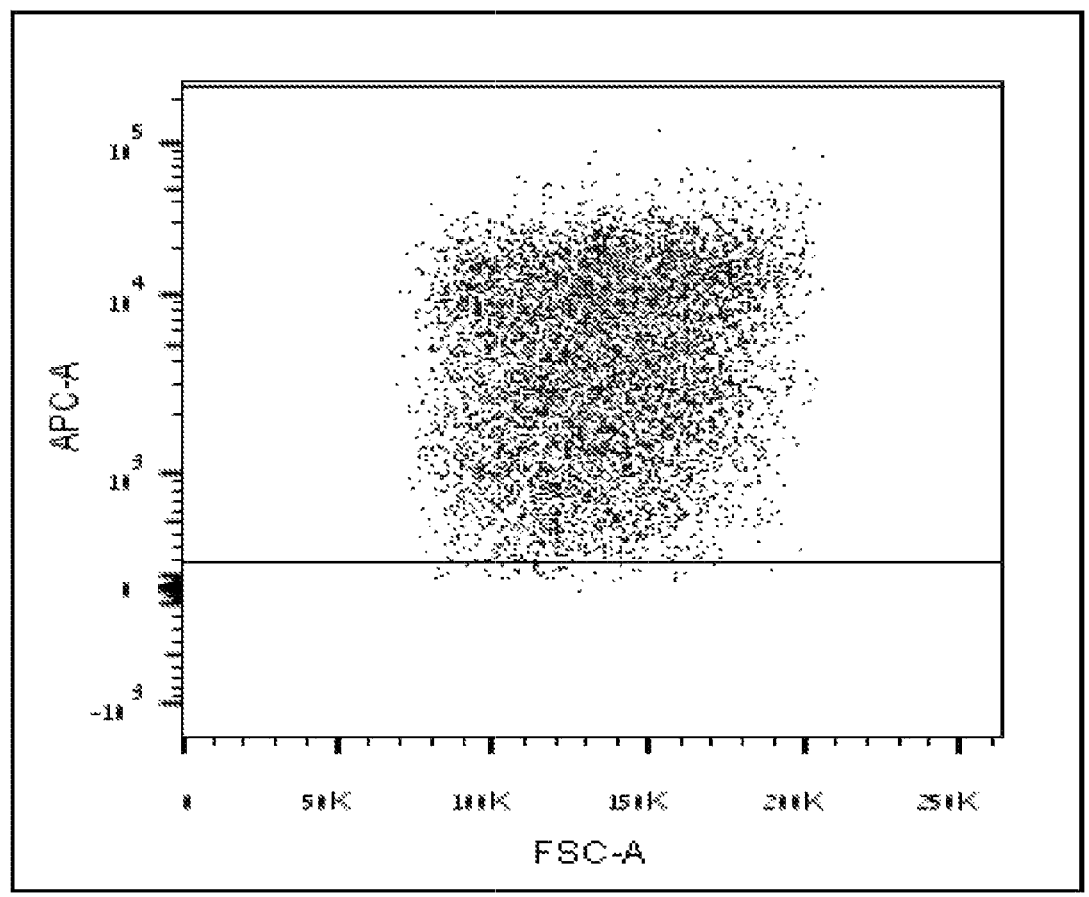
FIG. 1B is a FACS dot plot demonstrating binding percentage of FC-Rituximab, produced by papain digestion of rituximab, to CD-16.
Figure 1C:
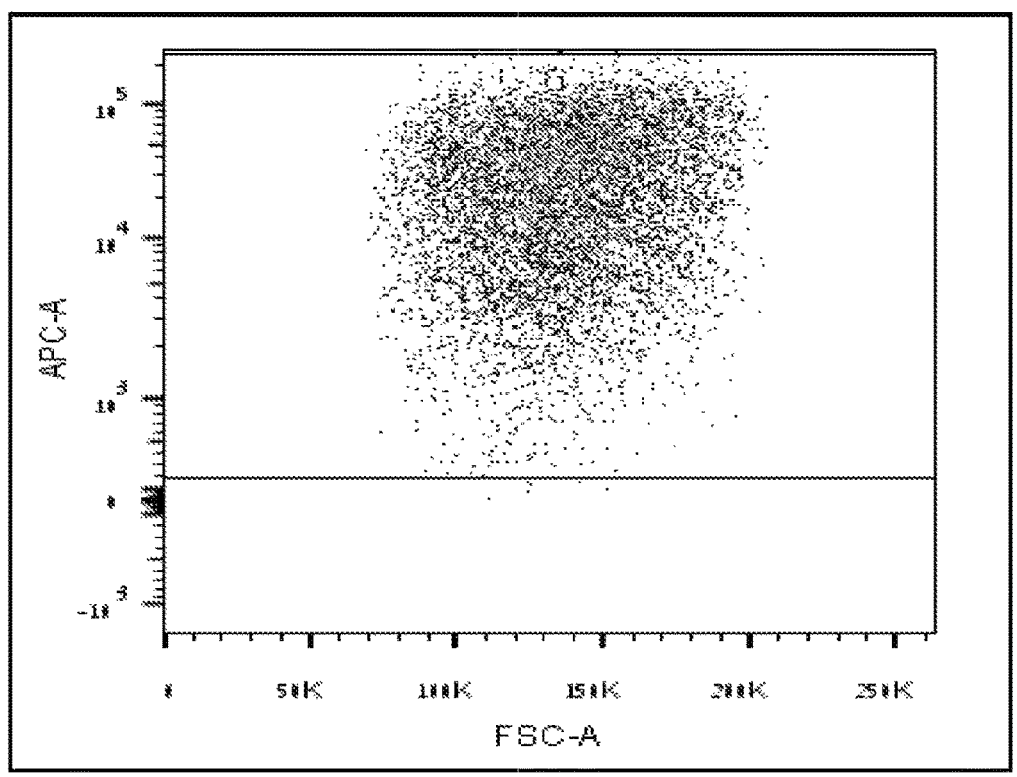
FIG. 1C is a FACS dot plot demonstrating binding percentage of intact rituximab to CD-16.
Figure 1D:
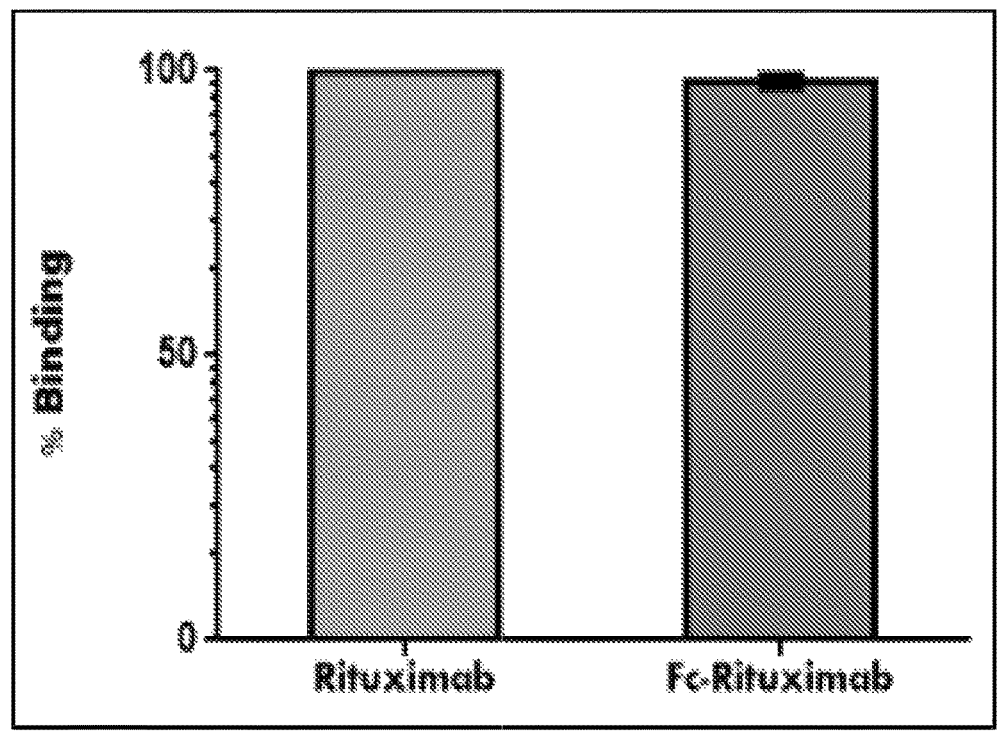
FIG. 1D is a bar graph comparing the binding percentage of Fc-rituximab and intact rituximab demonstrated in FIG. 1B and FIG. 1C, respectively.

Next, the affinity of the FC-Rituximab to CD-16 was evaluated. To this end intact rituximab and Fc-Rituximab, were incubated with BW-CD16 cells and binding percentage of intact rituximab and Fc-Rituximab to CD-16 were determined. FACS analysis demonstrated that the binding percentage of Fc-Rituximab to CD-16 (98.0±0.5, FIGS. 1B, 1D) was almost the same as the binding percentage of the intact rituximab to CD-16 (99.8±0.0, FIGS. 1C, 1D). This finding suggests that papain cleavage barely affected the binding efficiency.

Figure 1E:
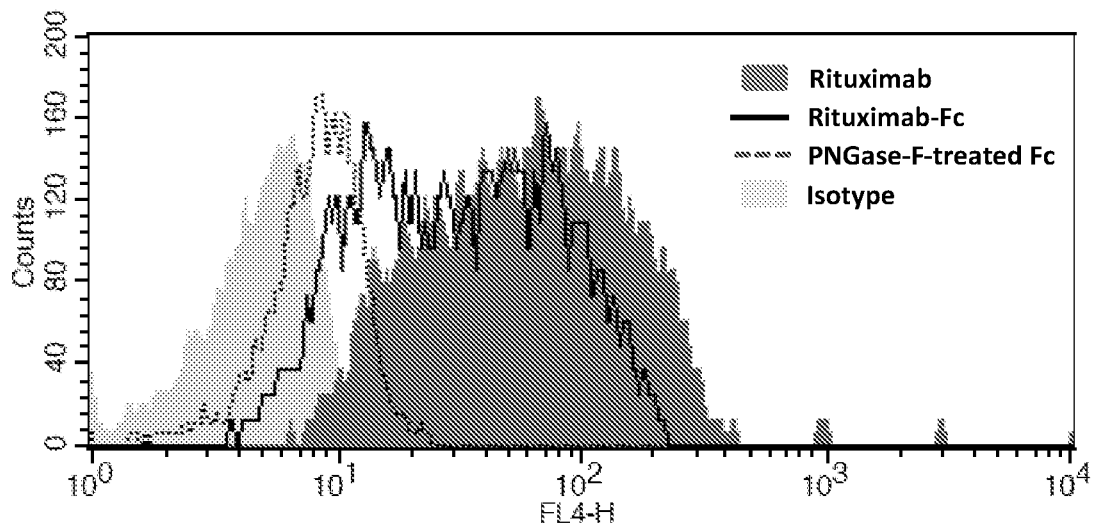
FIG. 1E is a plot showing evaluation of Fc specificity by coupling of (intact) rituximab or rituximab's Fc and PNGase-F-treated rituximab's Fc fragment to CD-16 BW cell line.
Figure 1F:
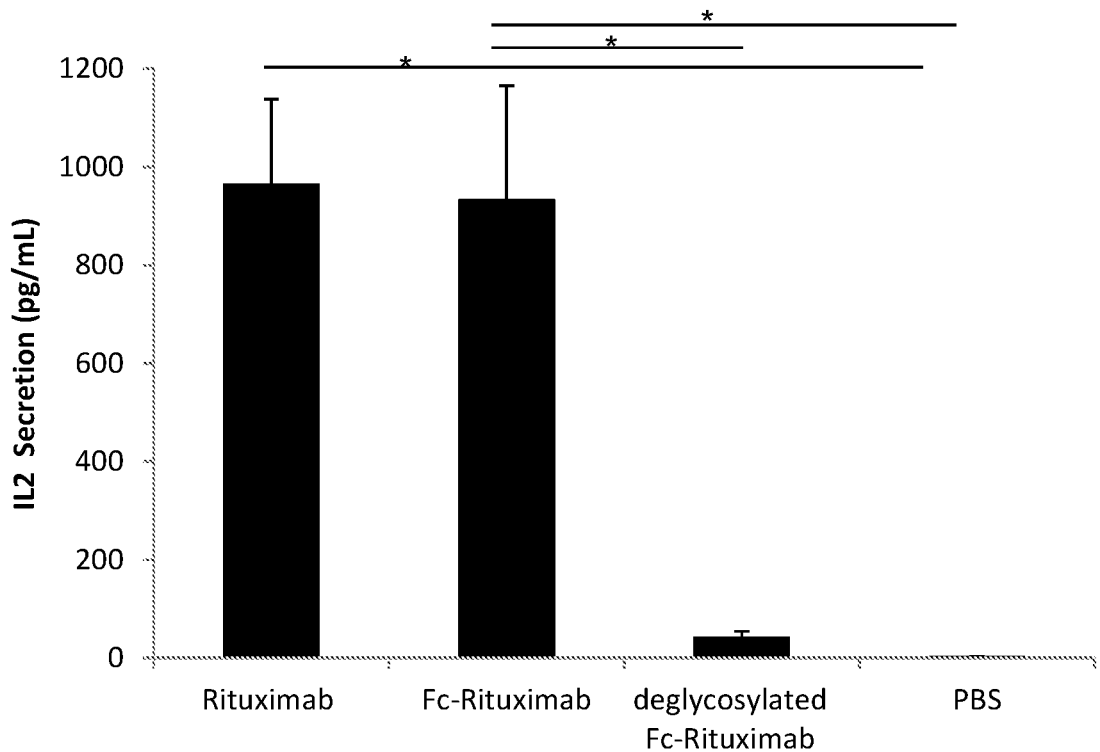
FIG. 1F is a bar graph showing secretion of IL-2 by BW cells in response to interactions with rituximab and rituximab's Fc fragment.

Specificity of the Fc was evaluated by coupling of (intact) rituximab or rituximab's Fc and PNGase-F-treated rituximab's Fc fragment to CD-16 BW cell line. Rituximab's Fc coupling to FcγRIIIA-transfected BW cell line resulted in secretion of cytokines; CD16-transfected BW cells were incubated overnight with intact or rituximab's Fc and PNGase-F-treated rituximab's Fc fragment in serum free RPMI. Isolated rituximab's Fc fragment had high affinity to CD16-transfected (BW) cells (FIG. 1E) and binds CD16 in a similar manner as ALS-IgG. Removing rituximab's Fc glycans decreased the interactions of Fc-CD16. As well, the formation of Fc-CD16 complex by rituximab or its Fc fragment and CD16-transfected BW cells stimulated IL-2 secretion in the same order of magnitude as ALS-IgG (FIG. 1F).

Figure 1G:
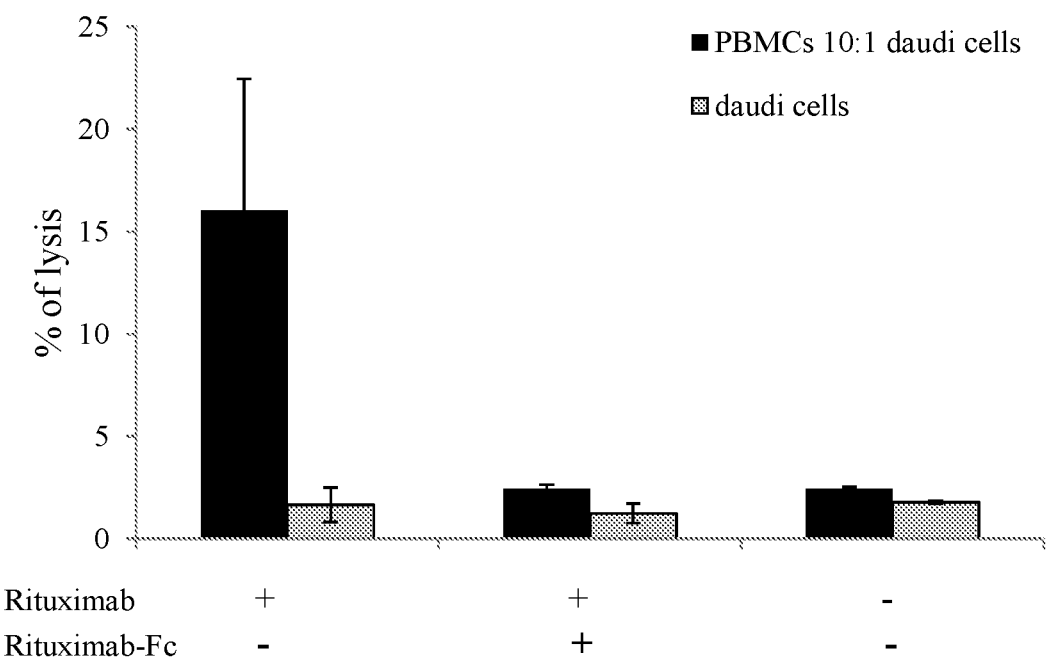
FIG. 1G is a bar graph showing killing B-cells through the antibody-dependent cellular cytotoxicity (ADCC), pathway by rituximab or rituximab Fc.

To assess the effect of rituximab's Fc on cytotoxicity an ADCC assay was performed using Daudi B-cells as target cells, PBMCs as effector cells, and intact rituximab as IgG sources. rituximab's Fc was used as an antagonist. Target cells, effector and IgGs were incubated for 5 h in serum free RPMI. MabThera Fc fragment blocked ADCC of Daudi B-cell line (these cells bear CD20) by CD16-transfected BW cells, relative to whole rituximab drug (FIG. 1G).

Taken together, these preliminary data indicate that the Fc fragment of rituximab is a partial antagonist of CD16, allowing cytokine secretion but blocking cell lysis.

Example 2

Fc-Rituximab Rescues Disease Phenotype of mSOD1$^{G93A}$ Mice

Figure 2A:
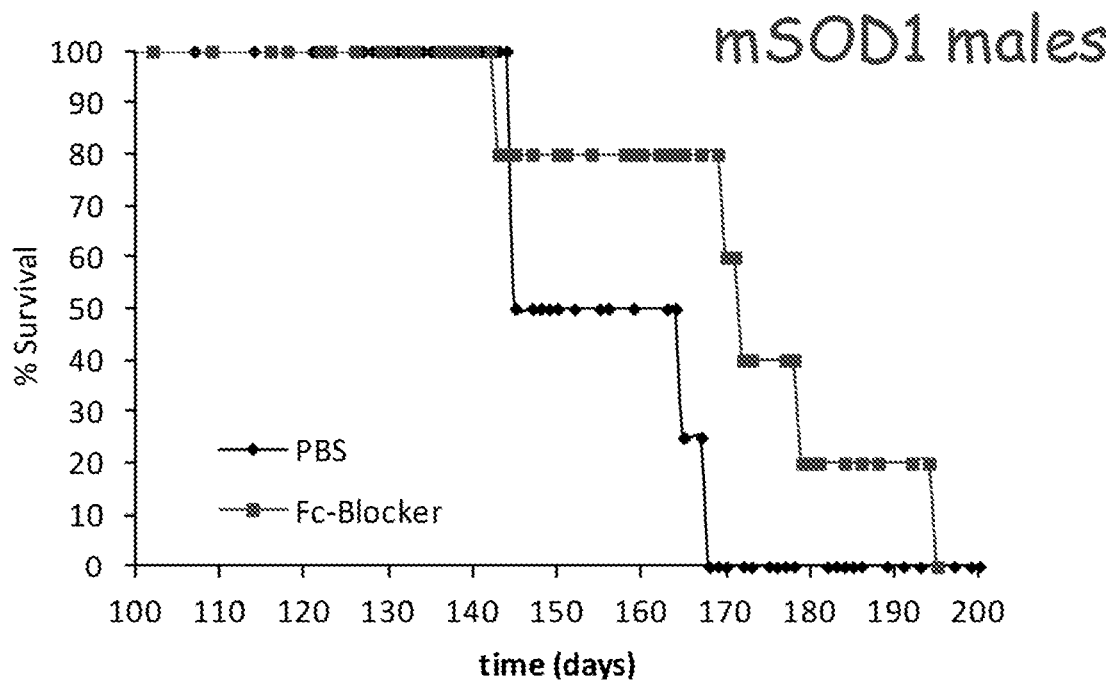
FIG. 2A is a graph showing the effect of rituximab or rituximab Fc injection on survival of mSOD1$^{G93A}$ mice.
Figure 2B:
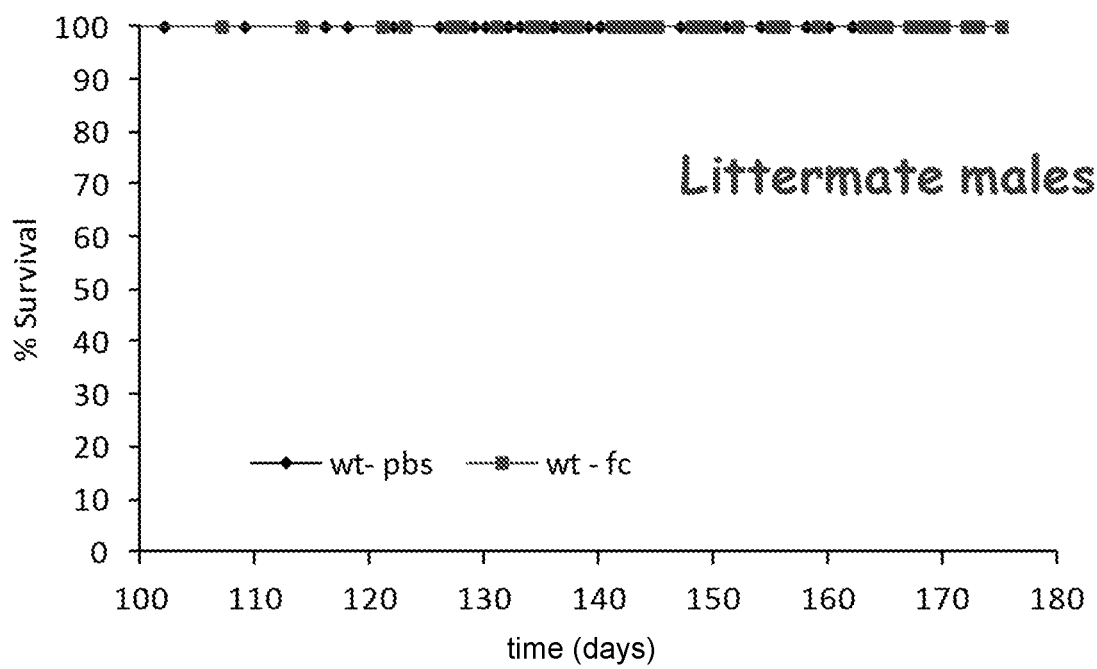
FIG. 2B is a graph showing the effect of rituximab or rituximab Fc injection on survival of littermate mice.
Figure 2C:
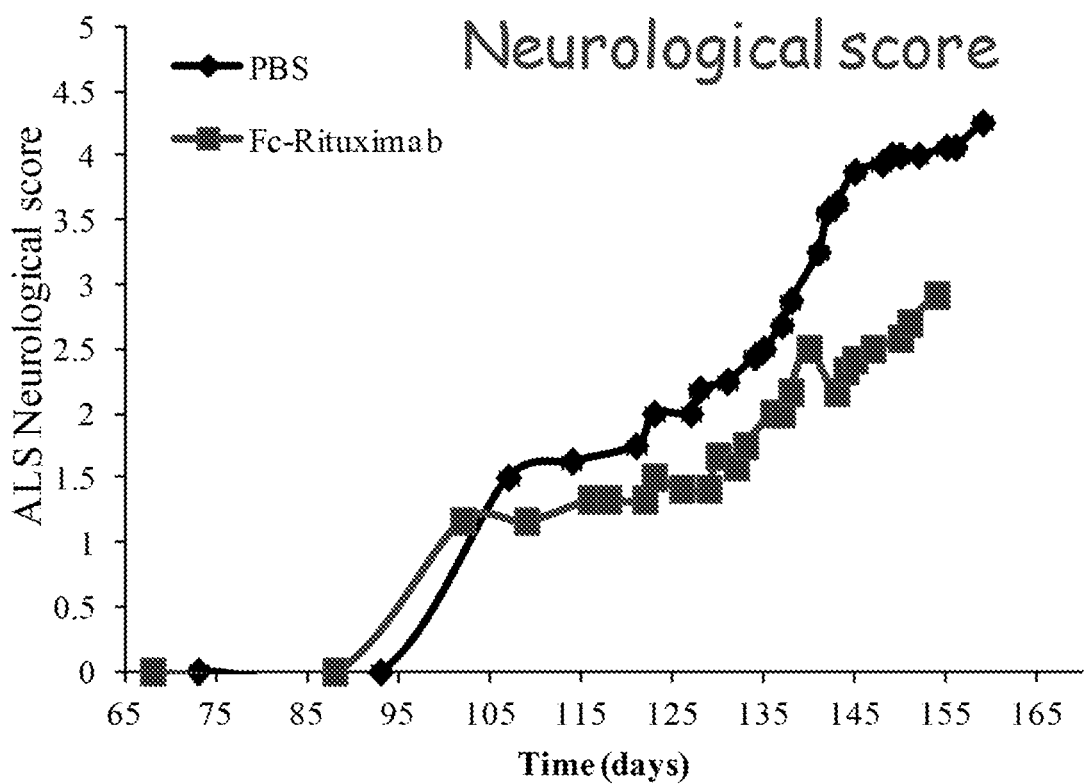
FIG. 2C is a graph showing the effect of rituximab or rituximab Fc injection on neurological score of mSOD1$^{G93A}$ mice.
Figure 2D:
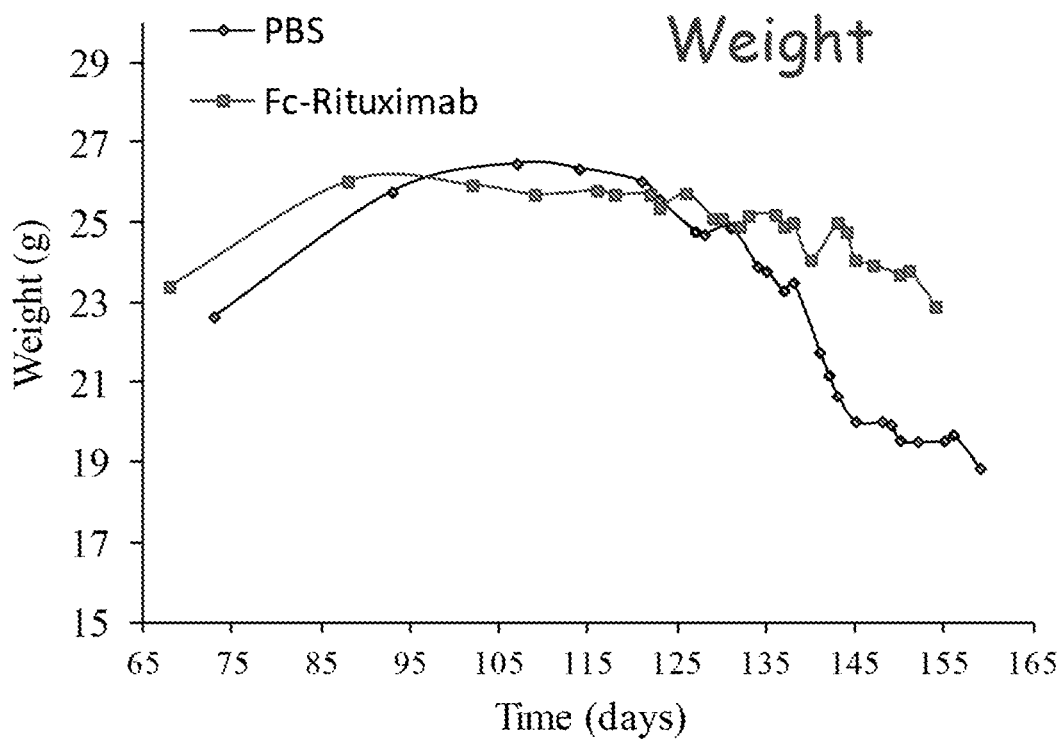
FIG. 2D is a graph showing the effect of rituximab or rituximab Fc injection on the weight of mSOD1$^{G93A}$ mice.
Figure 2E:
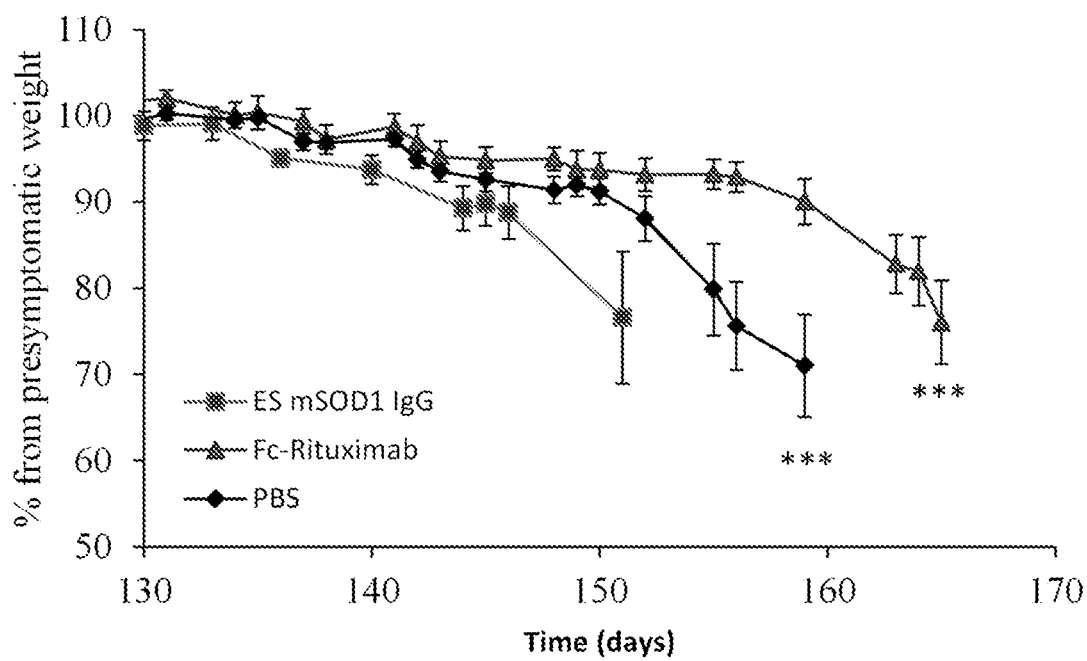
FIG. 2E is a graph showing loss of weight of 150 days IgG-treated mSOD1 mice compared to Fc-rituximab or PBS-treated mice.
Figure 2F:
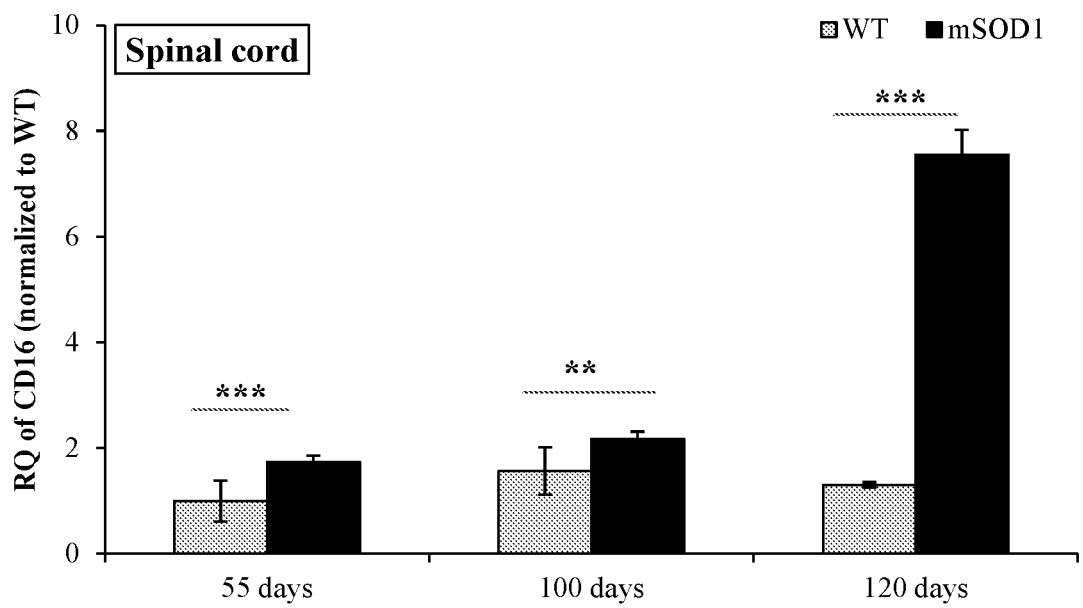
FIG. 2F is a bar graph showing CD16 expression in spinal cords of wild type (WT) and mSOD1$^{G93A}$ mice at different disease stages.
Figure 2G:
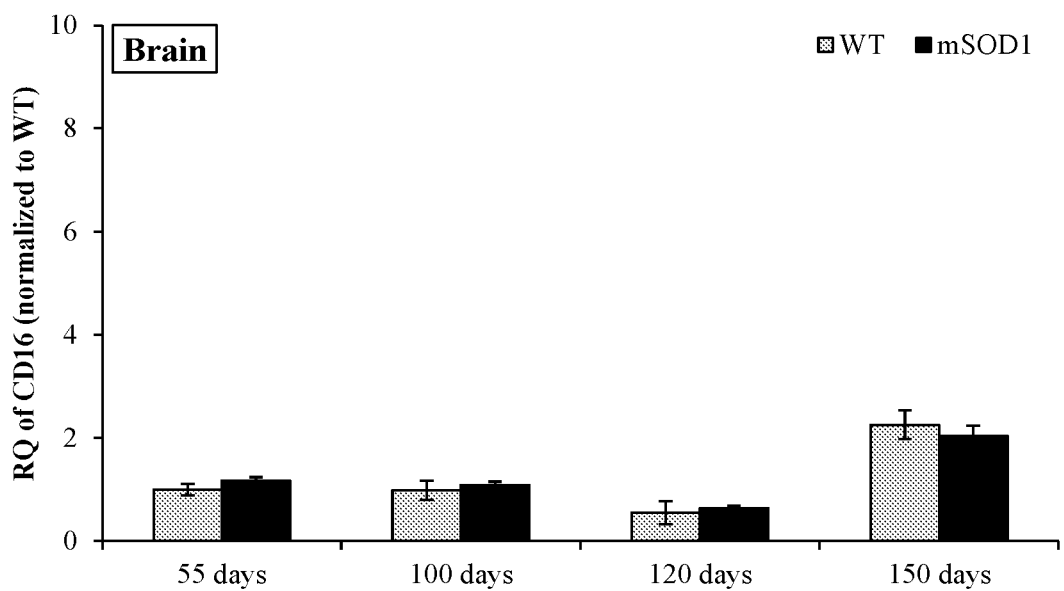
FIG. 2G is a bar graph showing CD16 expression in brains of WT and mSOD1$^{G93A}$ mice at different disease stages.

Fc-rituximab or PBS (placebo) were injected into cerebrospinal fluid (CSF) of pre-symptomatic 70 day old mSOD1$^{G93A}$ mice (n=15 of males and n=15 of females). Data showed that Fc-treated mice survived longer than PBS-treated mice (FIG. 2A). Littermates were not affected by PBS or Fc treatments (FIG. 2B). Also, body weight was better maintained in Fc-treated mice (FIG. 2D) and disease progression was decelerated relative to PBS-treated mice (FIG. 2C). Disease progression was measured by neurological score and was decelerated in Fc-rituximab a relative to PBS-treated mice neurological score: 0-presymptomatic stage; 5-fully paralysis, before death. Moreover, IgG antibodies of 150 day old mSOD1$^{G93A}$ mice (bearing the A2BG2 glycan) were injected into CSF of pre-symptomatic mSOD1$^{G93A}$ mice (n=5 of males and n=4 of females). The injected mice developed the disease two weeks earlier than untreated mSOD1$^{G93A}$ mice and significantly lost their weight as compared to Fc-MabThera or PBS-treated mice (FIG. 2E), indicating that IgG antibodies encompassing Fab domain with motor-neuron antigenic-binding site and Fc fragment with A2BG2 glycan deteriorate motor neuron abilities. Also, qRT-PCR analysis revealed CD16 mRNA increment in spinal cords of mSOD1 with disease progression and constant low expression in littermates (FIG. 2F). In contrast, the expression of CD16 in brains of mSOD1 mice and littermates at different disease stages was measured by mRNA extracted from the whole organ in quantitative real-time PCR. CD16 expression was similar and retained constant value during the disease, since mRNA was extracted from whole brain tissue, thus represents whole types of microglia cells (FIG. 2G).

Figure 3A:
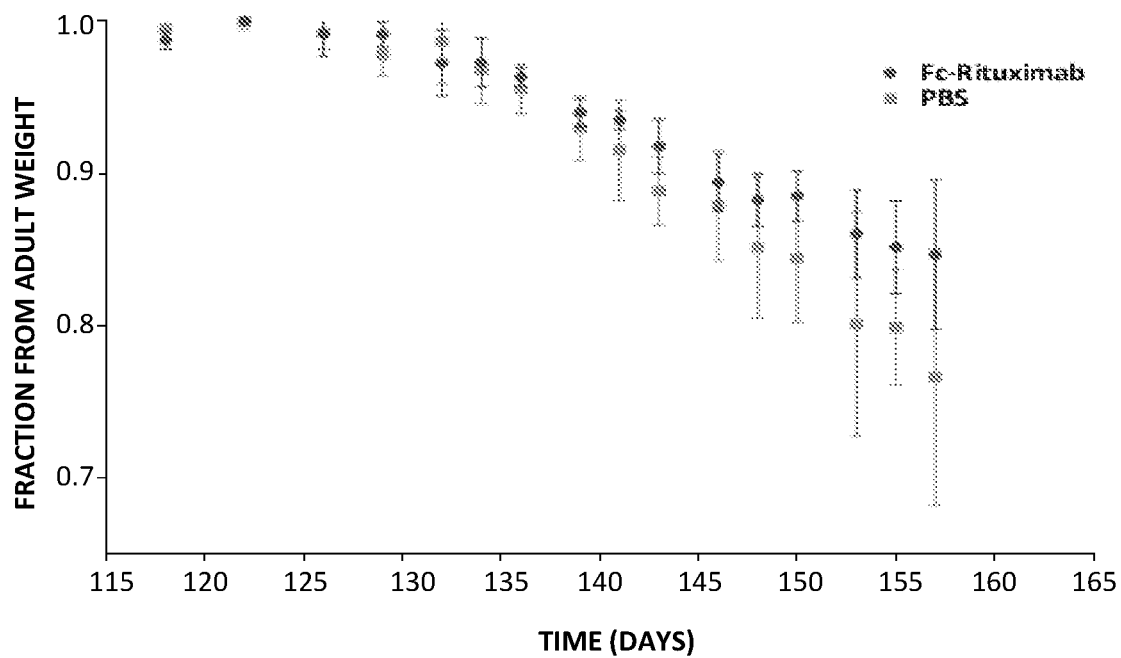
FIG. 3A is a graph comparing decline in body weight during disease progression of 70 days old mSOD1$^{G93A}$ male mice treated with either Fc-rituximab (n=3) or PBS (n=2).
Figure 3B:
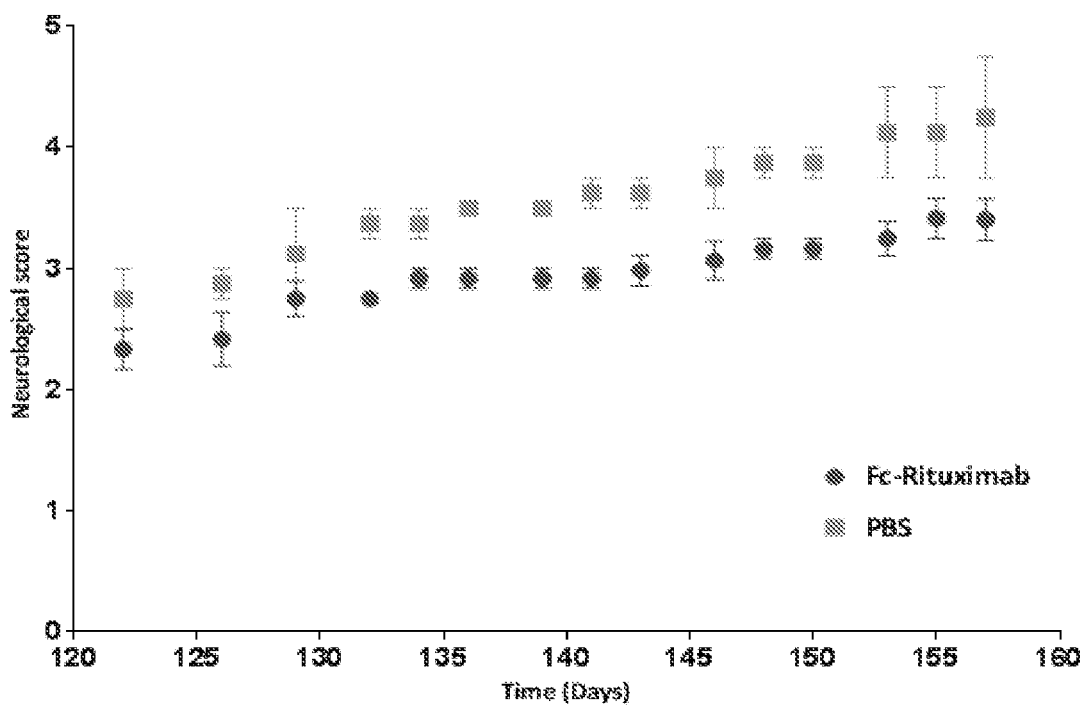
FIG. 3B is a graph comparing neurological scores during disease progression of 70 days old mSOD1$^{G93A}$ male mice treated with either Fc-rituximab (n=3) or PBS (n=2).

These experiments were duplicated using a smaller group of exclusively male mice. The measured decline in body weight (FIG. 3A) and the measured neurological score (FIG. 3b) corroborated the results of FIGS. 2C-E.

Example 3

Figure 4A:
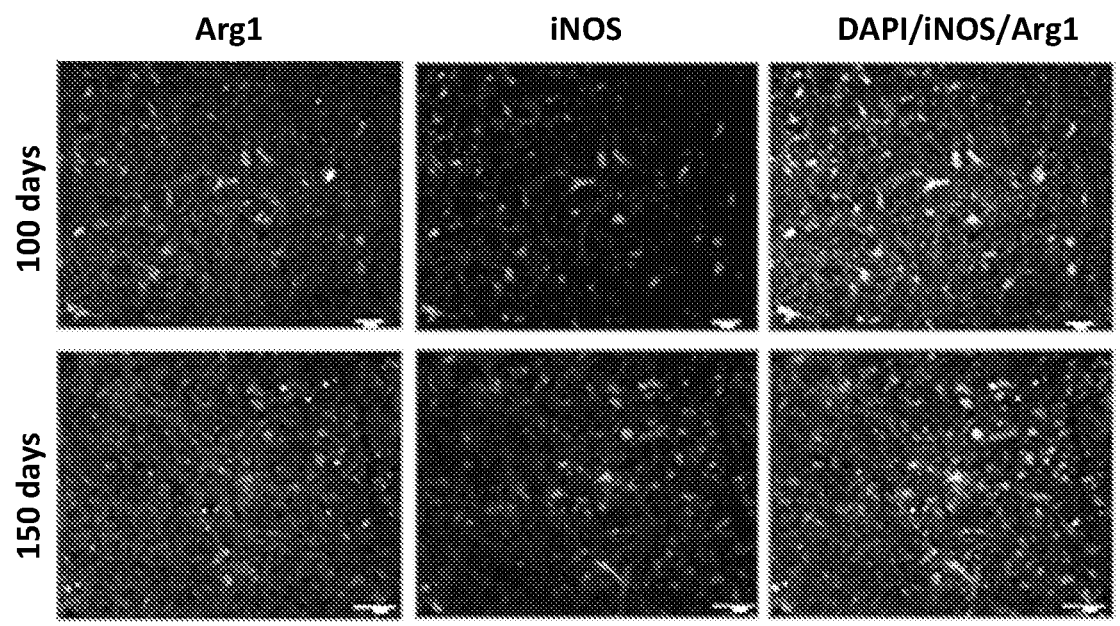
FIG. 4A are exemplary pictures showing iNOS (M1 marker) and Arg1 (M2 marker) and nuclear DAPIin mSOD1$^{G93A}$ brain
Figure 4B:
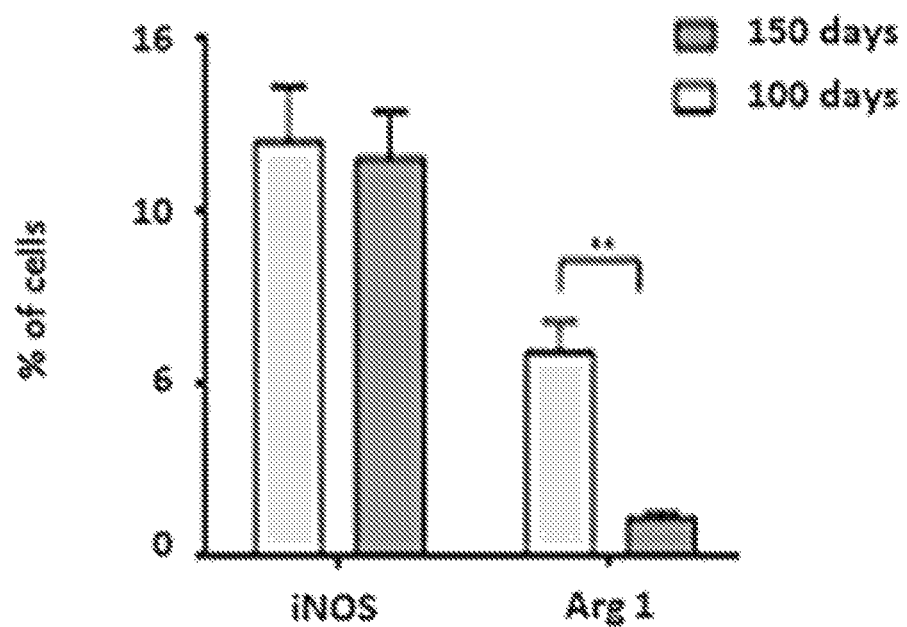
FIG. 4B is a graph showing M1 and M2 markers in mSOD1$^{G93A}$ brain at different disease stages.
Figure 4C:
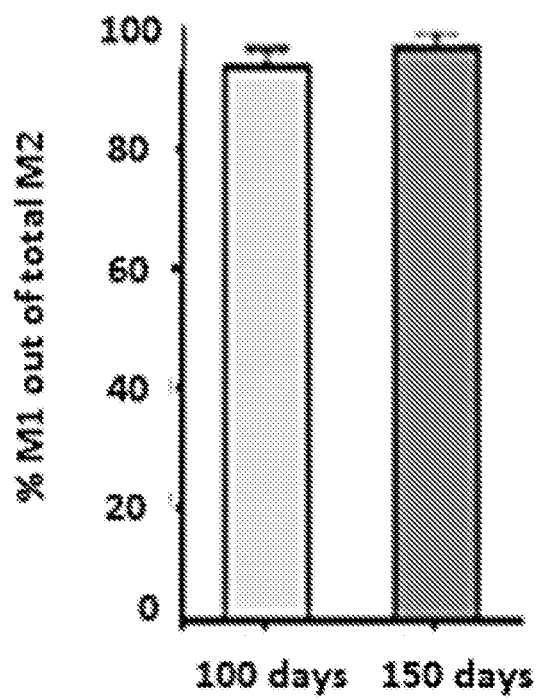
FIG. 4C is a graph showing expression of M1 marker on M2 cells at different disease stages.
Figure 4D:
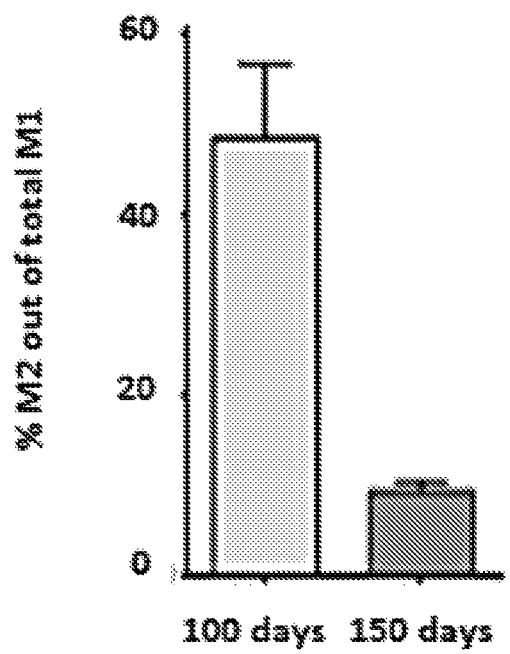
FIG. 4D is a graph showing expression of M2 marker on M1 cells at different disease stages.
Figure 5A:
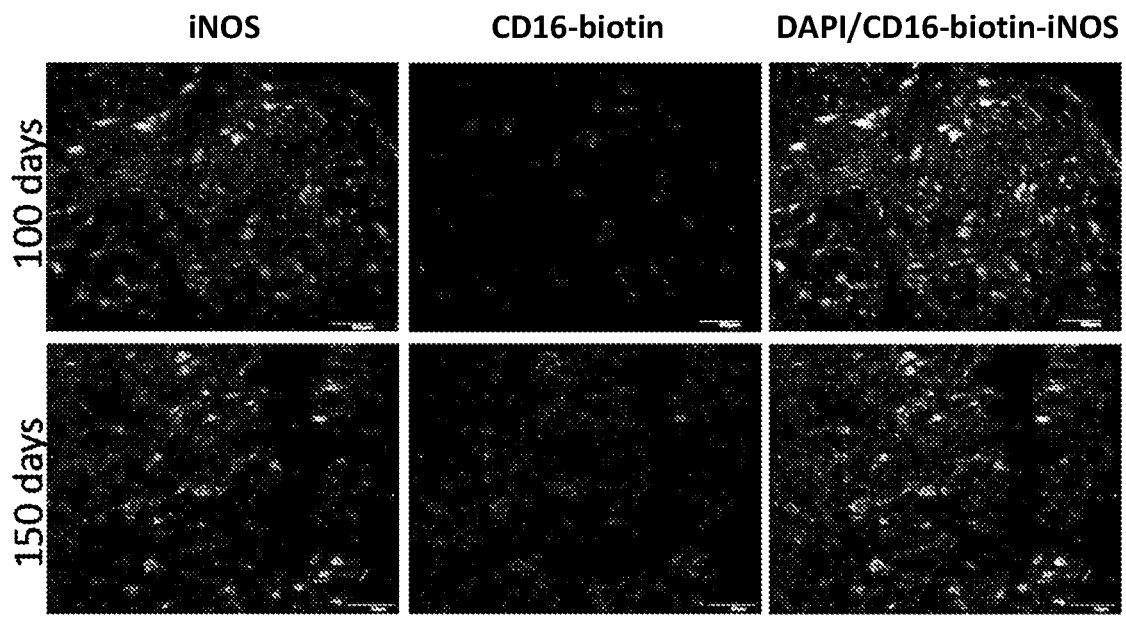
FIG. 5A are exemplary pictures showing Arg1 and CD16 expression levels on M1 microglia in mSOD1$^{G93A}$ brain
Figure 5B:
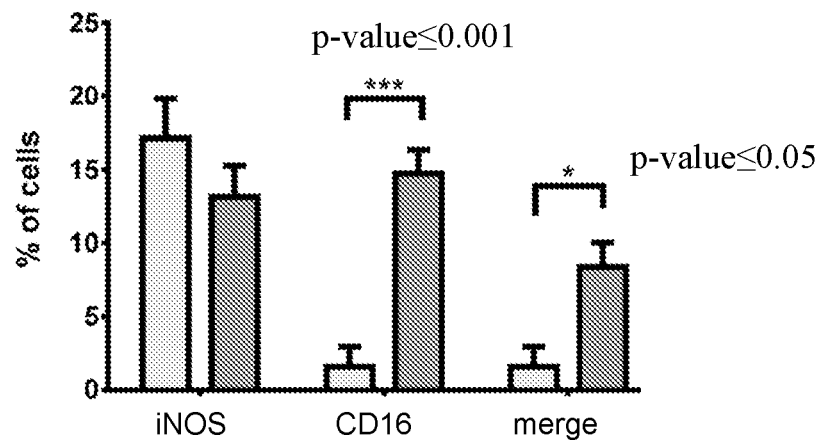
FIG. 5B is a graph showing Arg1 and CD16 expression levels on M1 microglia in mSOD1$^{G93A}$ brain at different disease stages.
Figure 5C:
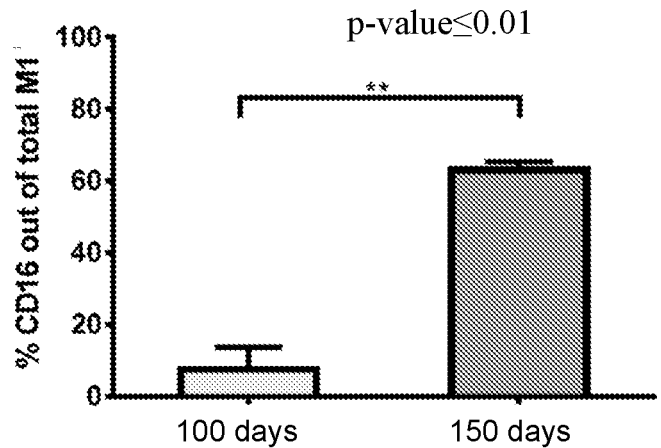
FIG. 5C is a graph showing percentage of CD16 positive cells out of total M1 microglia in mSOD1$^{G93A}$ brain at different disease stages.
Figure 6A:
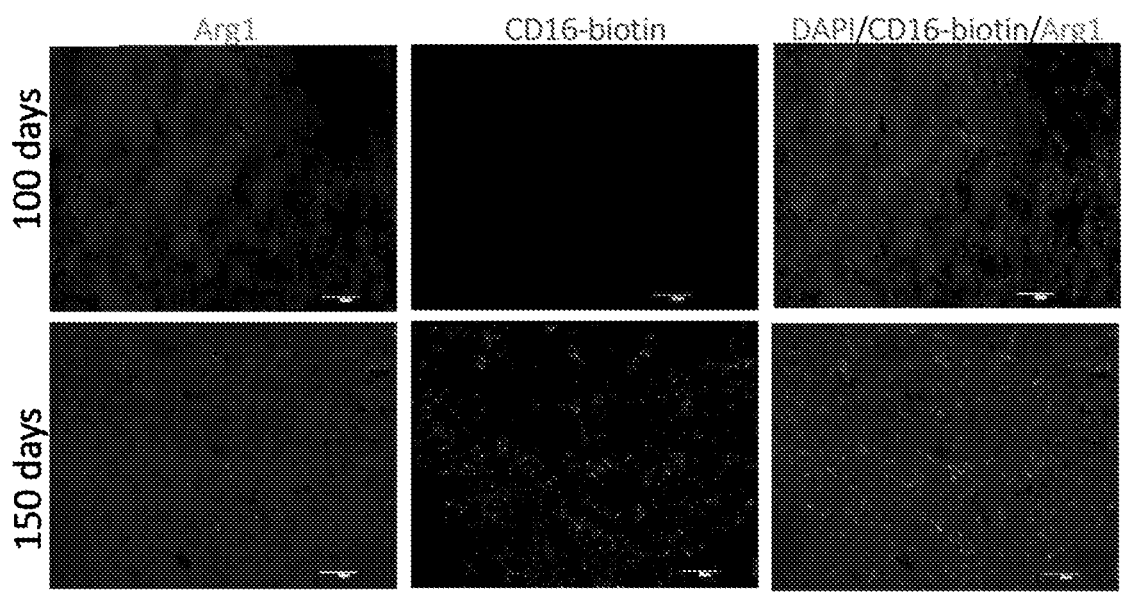
FIG. 6A are exemplary pictures showing Arg1 and CD16 expression levels on M2 microglia in mSOD1$^{G93A}$ brain
Figure 6B:
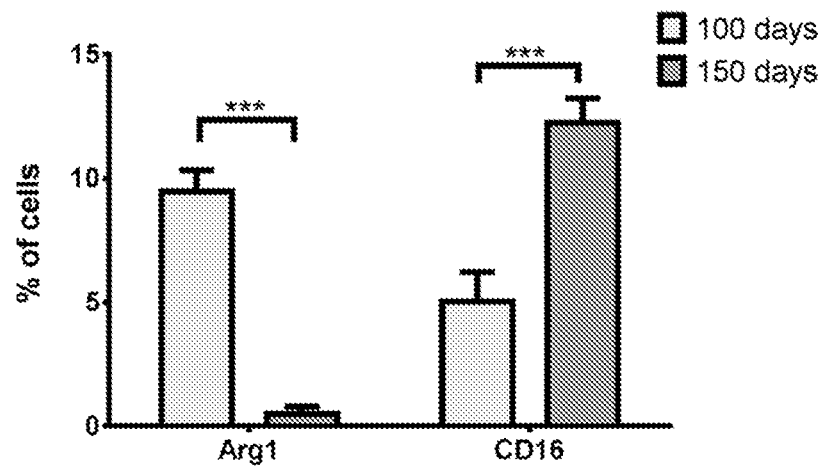
FIG. 6B is a graph showing Arg1 and CD16 expression levels on M2 microglia in mSOD1$^{G93A}$ brain at different disease stages.
Figure 6C:
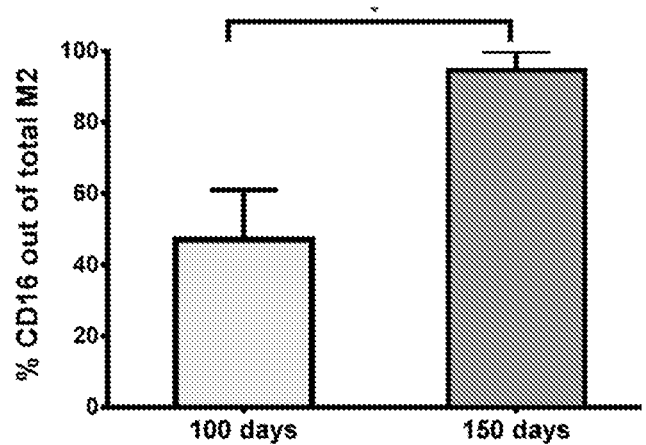
FIG. 6C is a graph showing percentage of CD16 positive cells out of total M2 microglia in mSOD1$^{G93A}$ brain at different disease stages.

Microglial Cells of mSOD1$^{G93A}$ Mice Express High Levels of CD16 Prior to Disease Onset Microglial cells of spinal cord and brain of 100 and 150 day old mSOD1$^{G93A}$ mice were double-stained for M1 (iNOS positive cells), M2 (arginase 1; Arg1 positive cells) and CD16. M1 microglial cells are mostly mediators of pro-inflammatory responses and cytotoxicity, whereas M2 cells, the anti-inflammatory population, emerge for resolution and cleanup. CD16 is known as a marker of M1. CD16 expression levels on M2 microglia in mSOD1 brain was measured. 150-day and 100-day old mSOD1 brain were stained for Arg1 (M2 marker), CD16, and nuclear DAPI. Scale bar-50 μm (FIG. 4A). Expression of M2 marker, CD16 and their co-expression in mSOD1 brain at different disease stages was measured (FIG. 4B). Expression of CD16 on M2 cells at different disease stages. 3 fields were counted for each group. (*-p-value≤0.05, ***-p-value≤0.001. Data represents mean±SEM) (FIG. 4C). Results show M1 in brain of mSOD1$^{G93A}$ mice at a similar number throughout the disease, while M2, which also appears at both disease phases, is significantly increased at the end of the disease. CD16 expression levels on M1 microglia in mSOD1 brain was measured. 150-day and 100-day old mSOD1 brain were stained for iNOS (M1 marker), CD16, and nuclear DAPI. Scale bar-50 μm (FIG. 5A). Expression of M1 marker, CD16 and their co-expression in mSOD1 brain at different disease stages was measured (FIG. 5B). Expression of CD16 on M1 cells at different disease stages. 3 fields were counted for each group (FIG. 4C) (*-p-value≤0.05, -p-value≤0.01, *-p-value≤0.001. Data represents mean±SEM). As expected, CD16 expression on M1 is enhanced at the end of the disease relative to disease onset CD16 expression levels on M2 microglia in mSOD1 brain was measured. To evaluate the expression levels of Arg1 and CD16 in mSOD1$^{G93A}$ mice 150-day and 100-day old mSOD1 brain were stained for Arg1 (M2 marker), CD16, and nuclear DAPI. Scale bar-50 μm (FIG. 6A). Expression of M2 marker, CD16 and their co-expression in mSOD1 brain at different disease stages was measured (FIG. 6B). Expression of CD16 on M2 cells at different disease stages. 3 fields were counted for each group was measured (FIG. 6C) (*-p-value≤0.05, ***- p-value≤0.001. Data represents mean±SEM). As can be seen, 40% of the M2 population at disease onset expresses CD16 and 100% of the 3% M2 at the end of the disease.

This data indicates that M2 population bearing CD16 plays cytotoxic or pro-inflammatory roles that injure neuron abilities. Thus, although ADCC takes part at the end of the disease, microglia cells can deteriorate neuron abilities at disease onset or even before.

Example 4

Effect of Fc-Rituximab on Neurons

Neurons of spinal cord and brain of 136 day old mSOD1$^{G93A}$ mice treated with Fc-Rituximab or PBS, were double-stained for NeuroN (for labeling neurons) and nuclear Dapi (4',6-diamidino-2-phenylindole) and confocally imaged.

Representative confocal microscopic images of brain (7A-F) and SC (7G-L) show a decrease in neurodegeneration (NeuN-) in both brain (7A-C) and SC (7G-I) sections of mSOD1$^{G93A}$ mice treated with Fc-Rituximab in comparison to PBS.

Example 5

Distribution of Fc-Rituximab in Mice's Brains

The distribution of Fc-Rituximab in the brains of wild type and mSOD1$^{G93A}$ mice was examined. To this end, mice were subjected to in vivo fluorescence using IVIS imaging 2.5 hours after injection of labeled Fc-Rituximab with Alexa Fluor 680.

Figure 8:
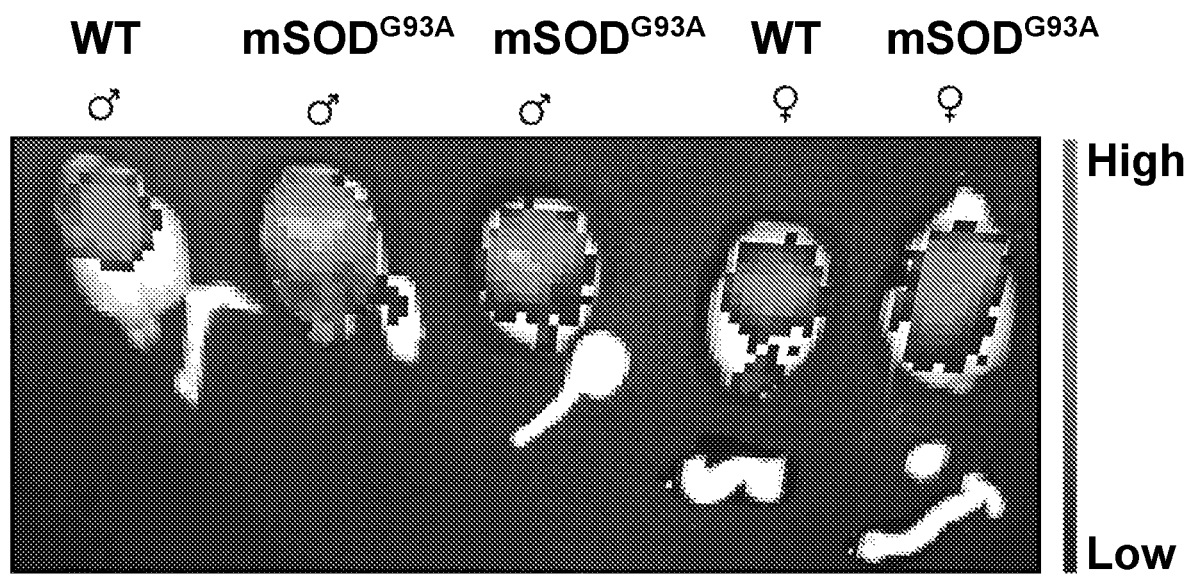
FIG. 8 shows distribution of the Fc-rituximab in mice brains 2.5 hours following injection of labeled Fc-rituximab with Alexa Fluor 680. Brains from mSOD1$^{G93A}$ mice showed a higher signal intensity in comparison to WT mice brains in both male and female.

As seen in FIG. 8, brain from mSOD1$^{G93A}$ mice showed a higher signal intensity in comparison to WT mice brain.

Example 6

Effect of Fc-Rituximab on Microglia Cytokine Secretion

Figure 9A:
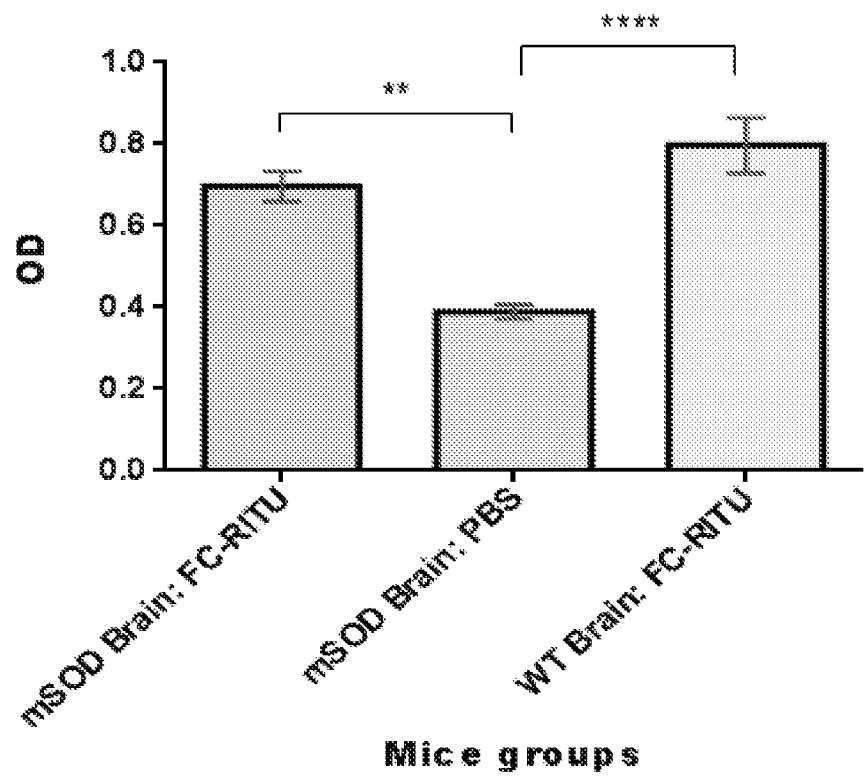
FIGS. 9A-9B are bar graphs showing TNF-alpha levels, as measured by Elisa, in cultured primary microglia cells obtained from brain (FIG. 9A) and SC (FIG. 9B) of mSOD1$^{G93A}$ and wild type mice treated with Fc-rituximab or PBS and sacrificed at 120 days old (n=6).
Figure 9B:
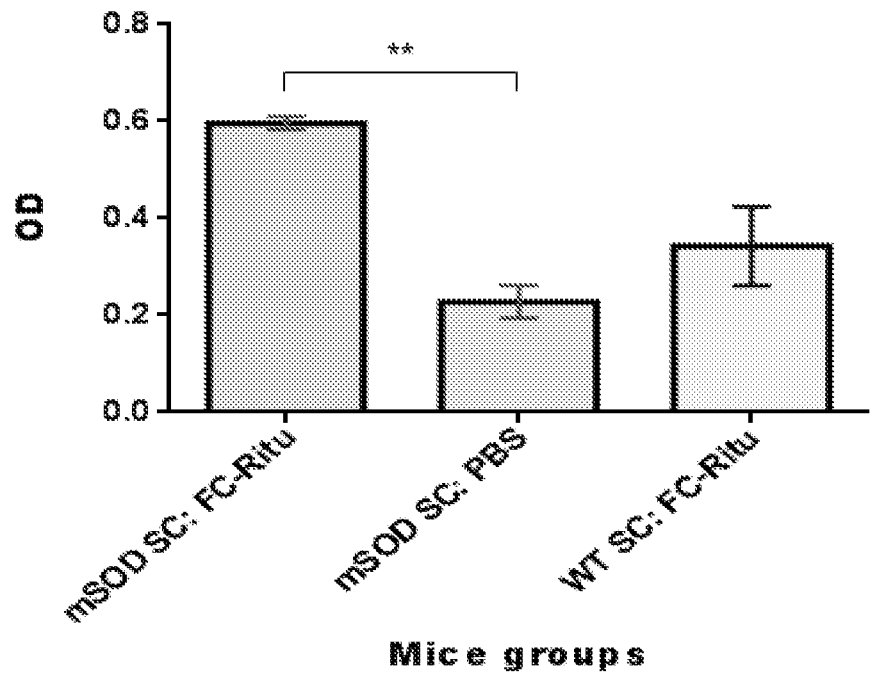

The effect of Fc-Rituximab on TNF-α release in cultured primary glia cells was evaluated. To this end, mSOD1$^{G93A}$ and WT mice were treated with Fc-Rituximab or PBS and sacrificed at 120 days old (n=6), and the levels of TNF-α were measured using ELISA kit. Results demonstrated increased TNF-α release in microglia cells treated with FC-Rituximab (FIG. 9A-B).

Further, the effect of various treatment including Rituximab, Fc-Rituximab and LPS on TNF-α release in cultured primary microglia cells was compared. To this end, in day 95 (disease onset), primary glia cells were isolated from brains of sacrificed mSOD1$^{G93A}$ mice, then incubated over night with RPMI medium supplemented with inactivated fetal bovine serum (Blank), Fc-Rituximab (0.12 mg/ml), intact Rituximab (1 mg/ml) or LPS (n=3), and the levels of TNF-α were measured using ELISA kit.

Figure 10:
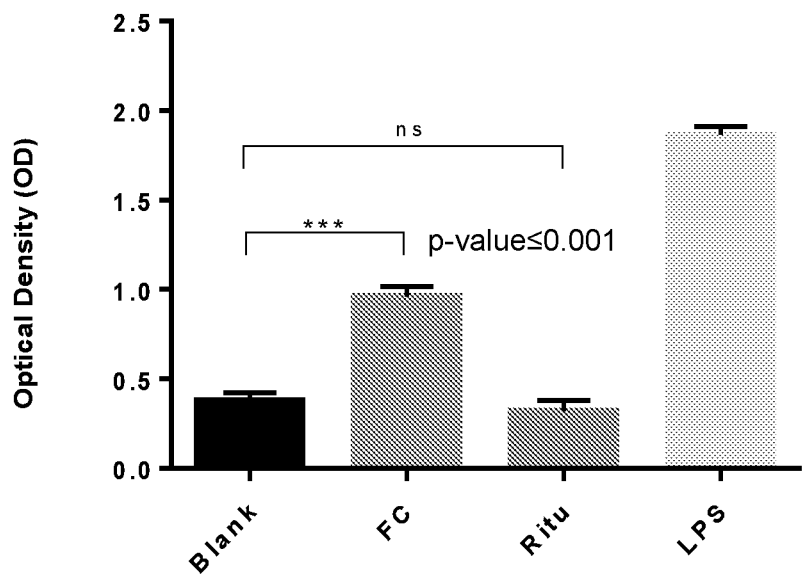
FIG. 10 is a bar graph showing TNF-α release in cultured primary microglial cells obtained from brains of sacrificed mSOD1$^{G93A}$ mice following various treatments (fetal bovine serum (Blank), Fc-Rituximab (0.12 mg/ml), intact Rituximab (1 mg/ml) or LPS).
Figure 11A:
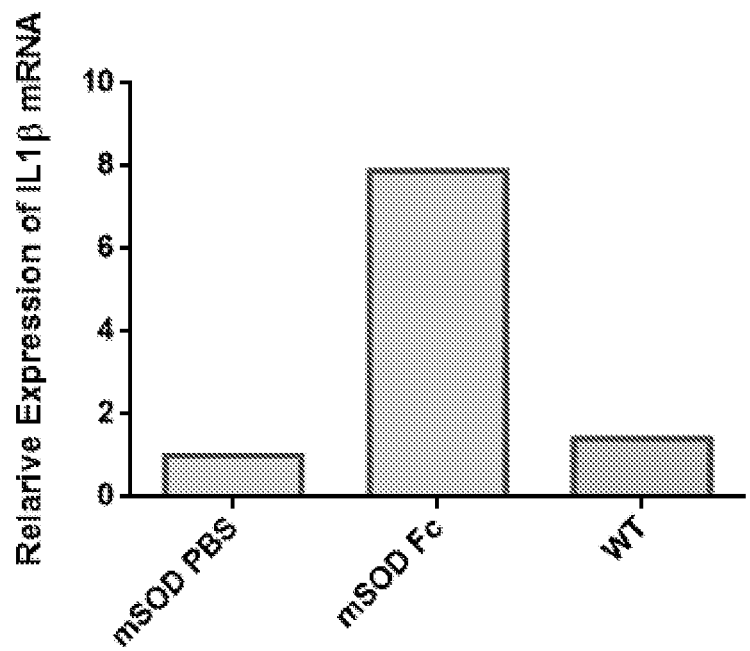
FIGS. 11A-11D are bar graphs showing CCL2 (FIG. 11A, 11B) and IL-1-beta (FIG. 11C, 11D) levels in microglia cells isolated from brains.
Figure 11B:
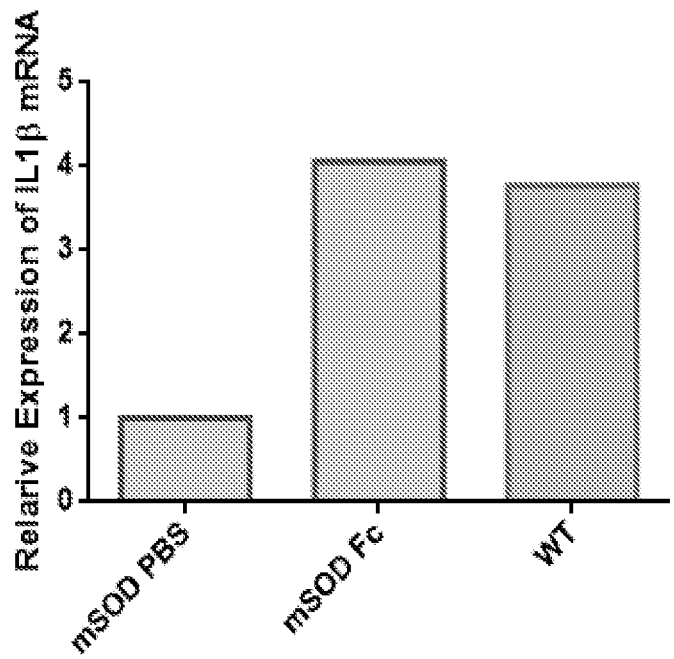
Figure 11C:
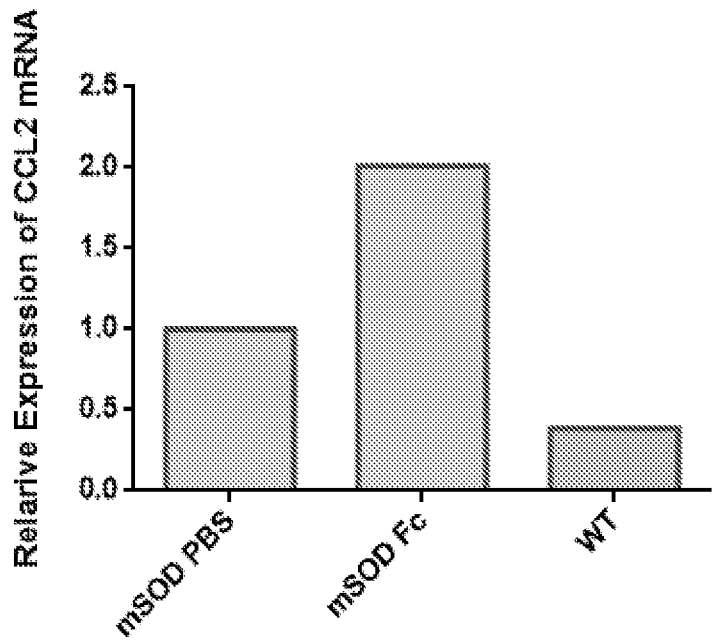
Figure 11D:
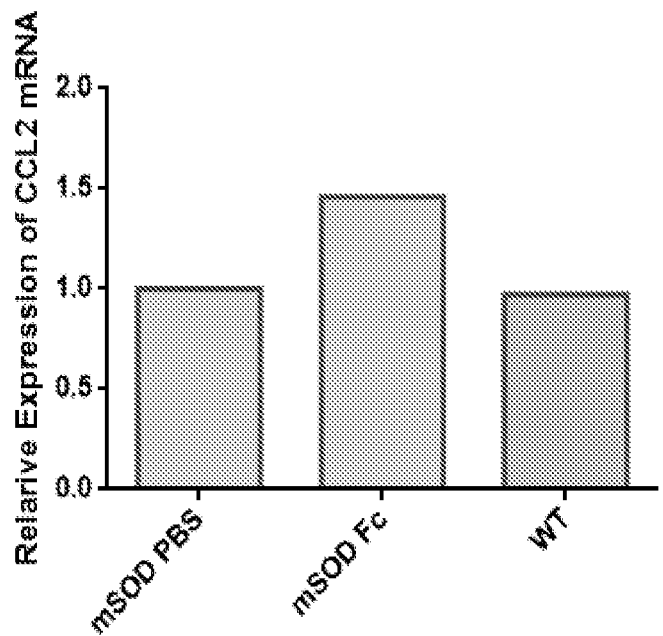

The results demonstrate increased TNF-α release in cultured primary microglia cells using Fc-Rituximab (FIG. 10).

Example 7

Gene Expression Profile in Microglia Cells after Fc-Rituximab Injection

In order to evaluate the expression of inflammatory genes, glia cells were isolated from both mSOD1 and WT mice 7 days after injection of Fc-rituximab or PBS. Inflammatory gene expression levels were analyzed by using qPCR, and TAQ-MAN primers. All samples were normalized to GAPDH housekeeping gene and to mSOD1 mice injected with PBS.

The results demonstrated an increase in IL-1 beta and CCL2 gene expression in brain (FIGS. 11 B and D) and an increase in IL-1 beta and CCL2 in spinal cord (FIGS. 11 A and C).

Example 8

The FC-Rituximab Improves Clearing Debris Activity of Microglial Cells

Figure 12A:
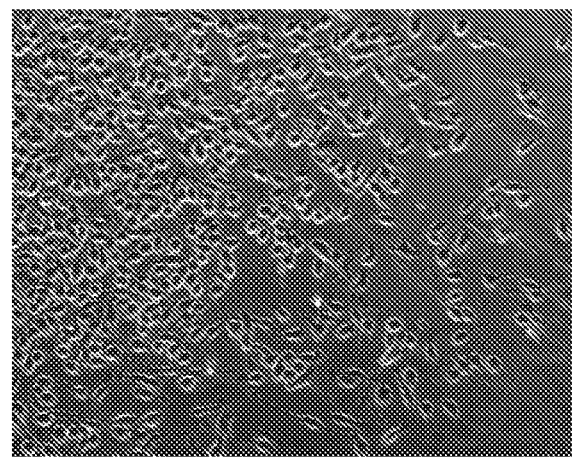
FIGS. 12A-12C are fluorescence microscopy images demonstrating phagocytosis of apoptotic NSC34 cells by microglia cell line (BV-2 cells) incubated for 16 h in RPMI medium supplemented with inactivated fetal bovine serum (Blank) (FIG. 12A), Fc-rituximab (0.116 mg/ml) (FIG. 12B) or intact rituximab (0.25-1 mg/ml) (FIG. 12C).
Figure 12B:
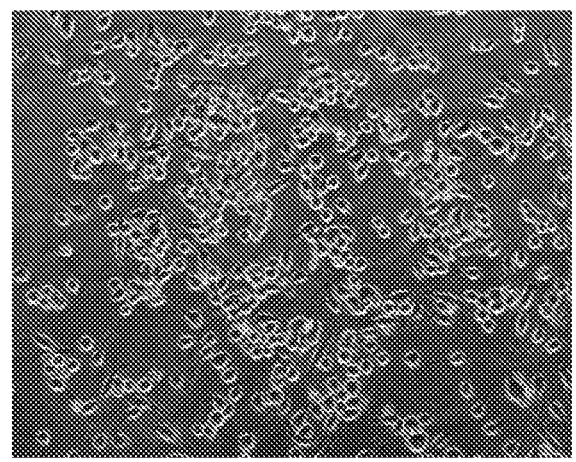
Figure 12C:
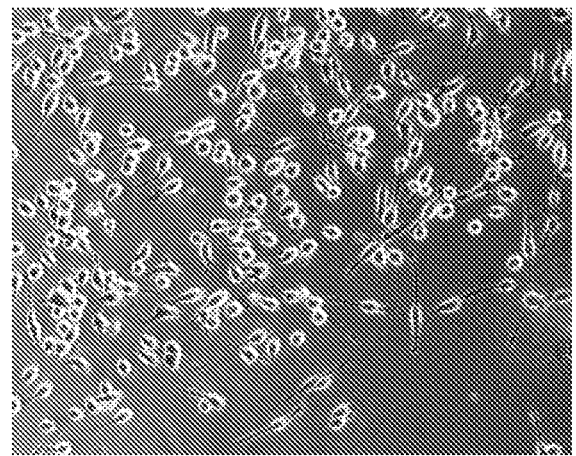
Figure 12D:
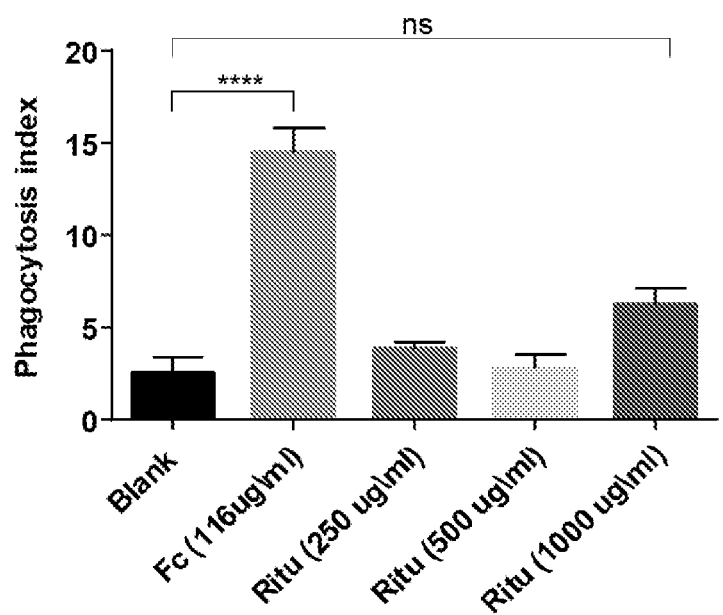
FIG. 12D is a bar graph showing the phagocytic index calculated according to FIGS. 12A-C.

In order to evaluate the effect of Fc-Rituximab on the phagocytic activity of microglial cells, phagocytosis of apoptotic NSC34 by cells of a microglial cell line (BV-2 cells) was examined. To this end, BV-2 cells were incubated for 16 hours in RPMI medium supplemented with inactivated fetal bovine serum (Blank), Fc-Rituximab (0.116 mg/ml) or different dilutions of intact Rituximab (0.25-1 mg/ml) (C). Next, apoptotic and stained motor neuron line of NSC34 cells were added to the BV-2 cells for additional 3 h. Intracellular staining was performed with CFSE and irradiation by UV until cells turned into apoptotic cells. Apoptosis was measured by 7AAD nuclei staining. Fluorescence microscope images were obtained (FIGS. 12A-C) and the phagocytic index was calculated by measuring the number of BV-2 cells with CFSE debris to total number of BV-2 cells per field (FIG. 12D).

The results demonstrated under FIGS. 12A-D show an increased phagocytic activity following incubation with Fc-Rituximab Example 9

Binding of Serum IgG to a Human Neuroblastoma and Mouse NSC34 Cell Lines and to Lymphocyte CD16

Figure 13A:
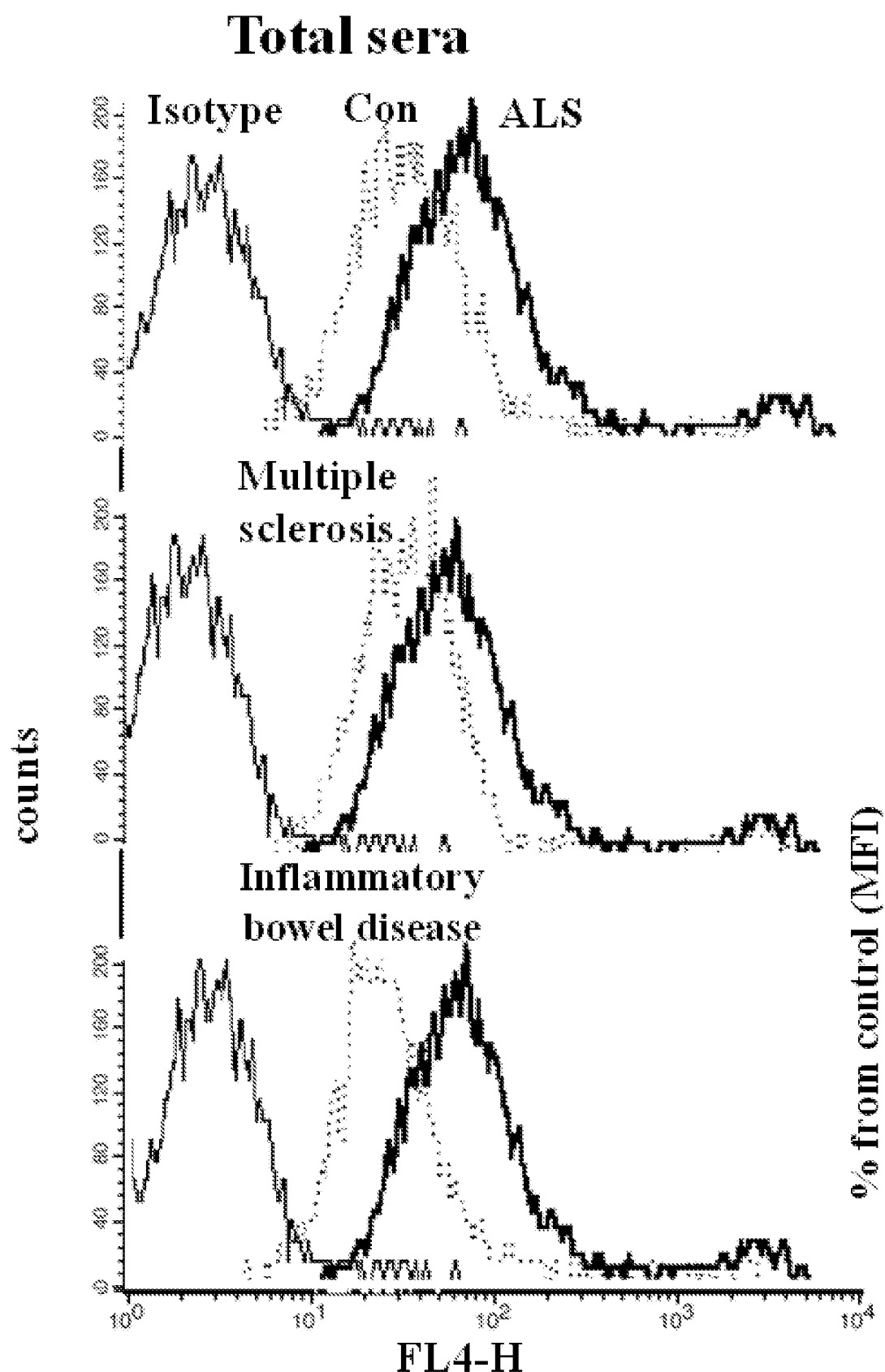
FIG. 13A is a FACS histogram presenting shift in binding of purified IgG from serum pools of ALS patients to neuroblastoma cells relative to binding of purified IgG from healthy control (CON).
Figure 13B:
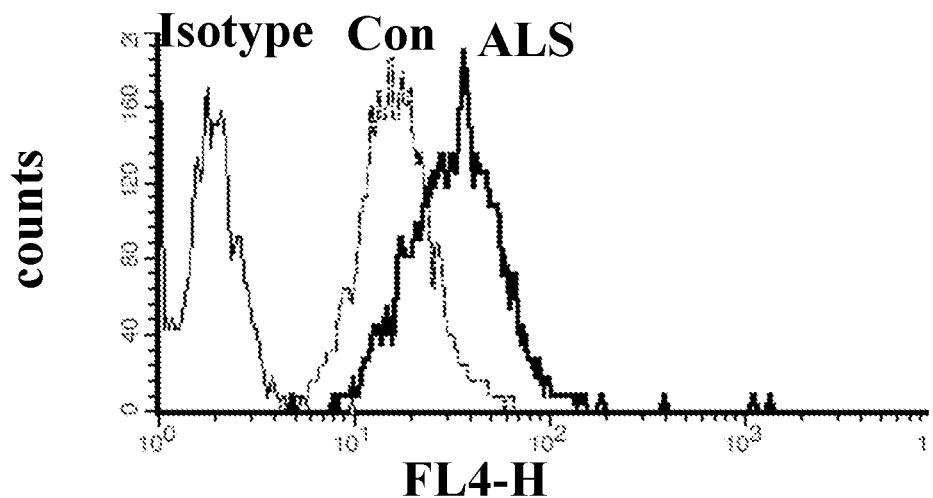
FIG. 13B is a FACS histogram presenting dose-dependent coupling of purified ALS-IgG to human PANC1, HeLa, and neuroblastoma cells performed as described in 13A.
Figure 13C:
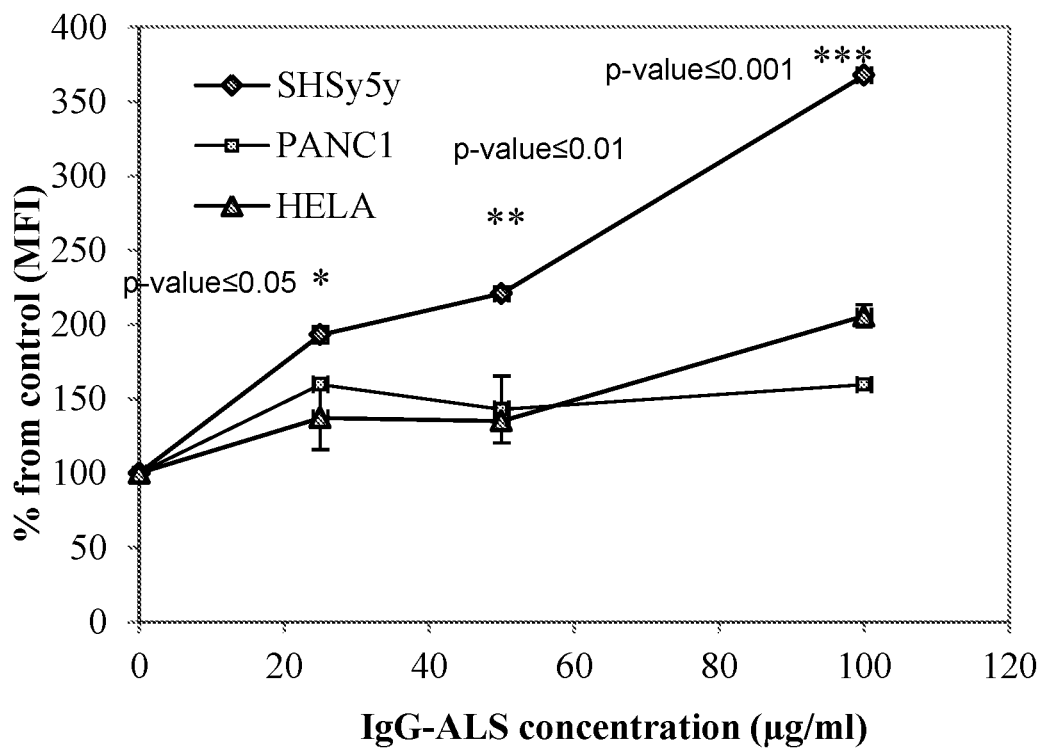
FIG. 13C is a graph showing mean fluorescent intensity (MFI) calculated relative to control sample containing cells and serum that was free of IgG. Dose-dependent coupling of ALS-IgG to mouse NSC34 cells was performed as described above.
Figures 13D, 13E:
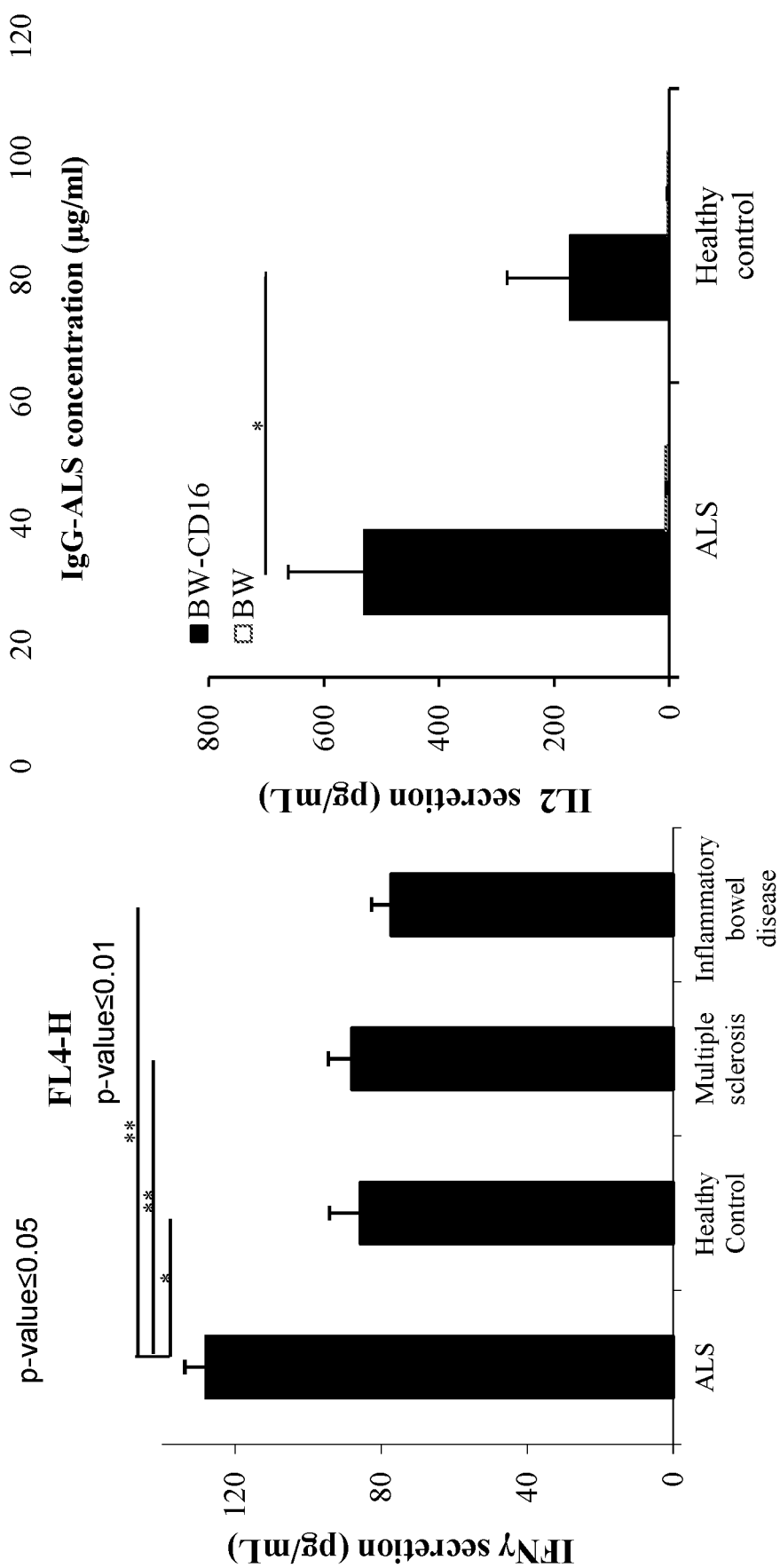
FIG. 13D is a bar graph showing secretion of IFNγ by enriched human peripheral NK cells in response to interactions with pools of ALS, inflammatory bowel disease patients, patients of multiple sclerosis, and healthy control (CON) sera.
FIG. 13E is a bar graph showing secretion of IFNγ by enriched human peripheral NK cells in response to interactions with ALS-IgG and ALS IgG-depleted sera.

Neurons can serve as antigenic targets for ALS-derived IgG, and that they poorly bind IgG from healthy controls or from inflammatory bowel disease or multiple sclerosis patient samples. As such, neuroblastoma cells blocked by anti-CD16/CD32 antibodies were incubated with pools of serum samples or with purified IgG and then assessed by FACS. The blocking step was performed only in the experiments of binding IgG to the target cells in order to reduce unspecific binding. The binding of either purified or unpurified ALS-IgG to the surface of the neuroblastoma cells was elevated, in comparison to such binding by pools of IgG from healthy control (FIGS. 13A, B), or by IgG pools from inflammatory bowel disease (FIG. 13A) or from multiple sclerosis patients (FIG. 13A). Comparing the specificity of ALS-IgG binding by neuroblastoma, HeLa and PANC1 cells revealed significant differences between neuronal and non-neuronal cells (FIG. 13C). To confirm the latter result but with the appropriate target cell, binding experiments were repeated using neuroblastoma-spinal cord motoneuron hybrid cell line, NSC34 exposed to different serum concentration. As opposed to neuroblastoma, NSC34 cells bound ALS-IgG in a similar manner as they bound IgGs from healthy controls (FIG. 13D). This is particularly important when demonstrating the cytotoxic effects of IgGs via their coupling to CD16 in the ADCC reaction.

Figure 13F:
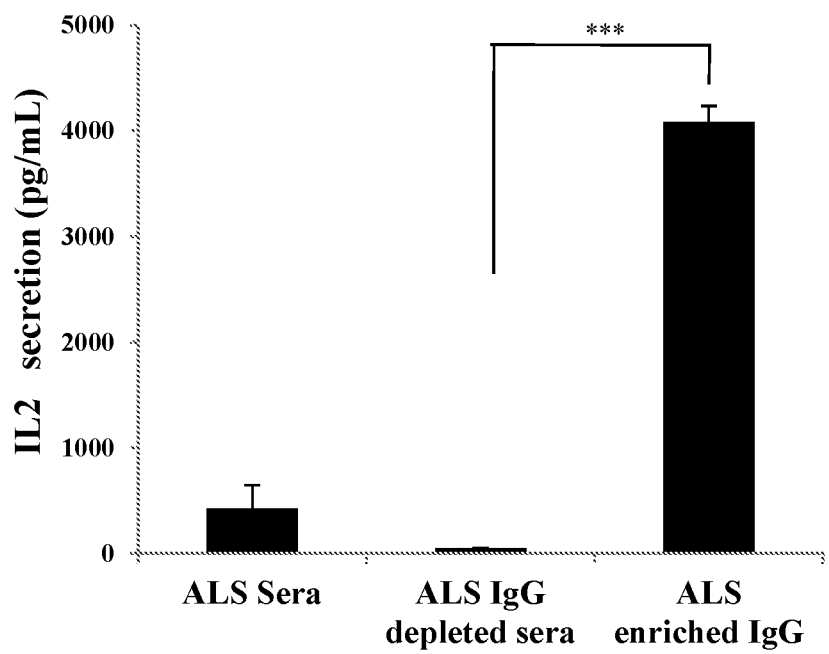
FIG. 13F is a graph comparing the specificity of dose-dependent coupling of PNGase F-treated or untreated IgG of ALS patients and of the IgG of healthy volunteers, to CD16.
Figure 13G:
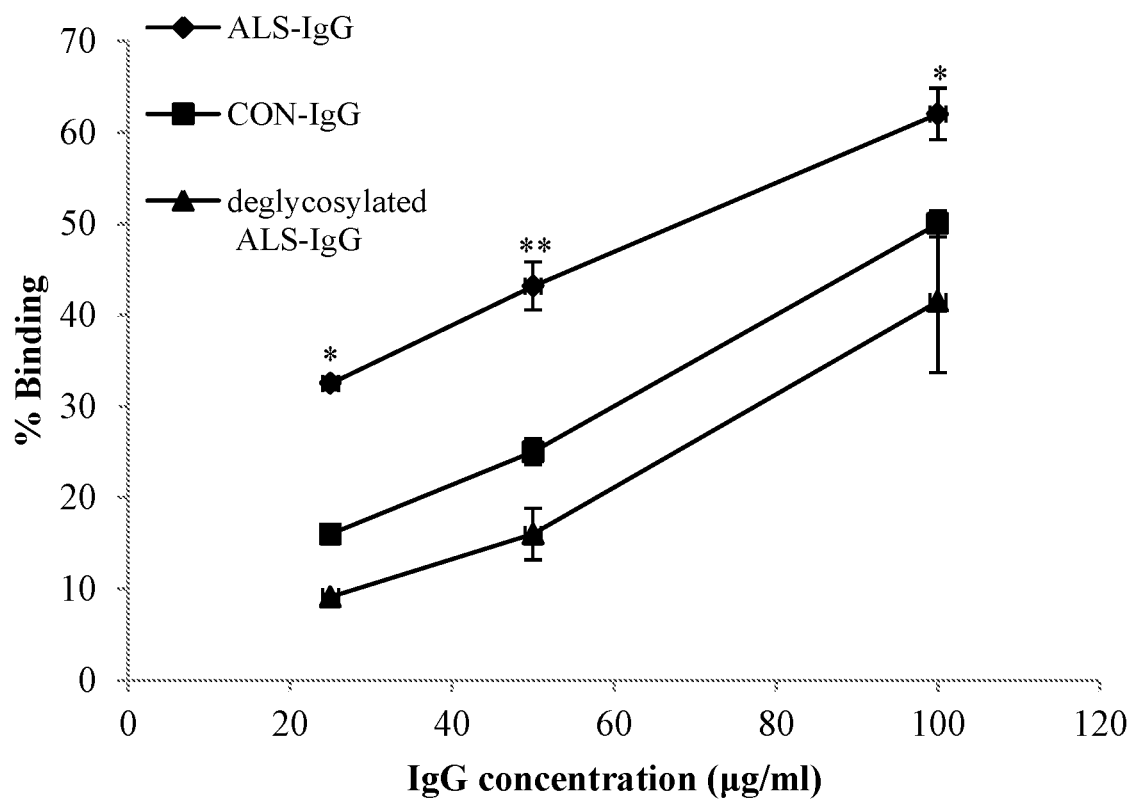
FIG. 13G is a graph showing % Binding vs. IgG concentration in response to ALS IgG-depleted sera.

Analysis of the effect of elevated amounts of A2BG2 glycan in the Fc domain found in ALS-IgG on the affinity of these antibodies to CD16. This was done by measuring cytokine production and the percentage of IgG binding to CD16. Pools of serum samples from healthy controls, ALS, from patients with inflammatory bowel disease and from multiple sclerosis patients, containing similar concentrations of IgG were incubated with purified human peripheral NK cells for 18 h. In addition, pools of serum samples from healthy controls and ALS or ALS-IgG and ALS IgG-depleted sera were incubated with BW-CD16-transfected or normal BW cells (26), for 18 h. NK cells containing CD16 and BW-CD16 transfectants produced IFNγ and IL-2, respectively, in response to Fc ligand coupling. ELISA results demonstrated that NK cells were activated by ALS patient sera to produce augmented amounts of IFNγ, while inflammatory bowel disease patient, multiple sclerosis patient or healthy control sera induced lower IFNγ production (FIG. 13E). Moreover, more than double the amount of IL-2 was produced by BW-CD16 transfectants in response to ALS patient sera, as compared to healthy control sera, while normal BW cells incubated with any sera did not produce IL-2 (FIG. 13F). In response to purified IgG, BW-CD16 transfectants produced more than 8-fold amount of IL-2, whereas negligible amounts of IL-2 were produced in response to ALS IgG-depleted sera (FIG. 13G). Examination of the specific coupling to CD16 of PNGase F-treated or untreated ALS-IgG or of IgG of healthy volunteers by FACS and several dilutions, revealed significant differences between the IgG containing the A2BG2 glycan to those lacking this glycan (FIG. 13H).

Example 10

Loss of Human Neuroblastoma and Mouse NSC34 Cells Through the ADCC Pathway

Figure 14A:
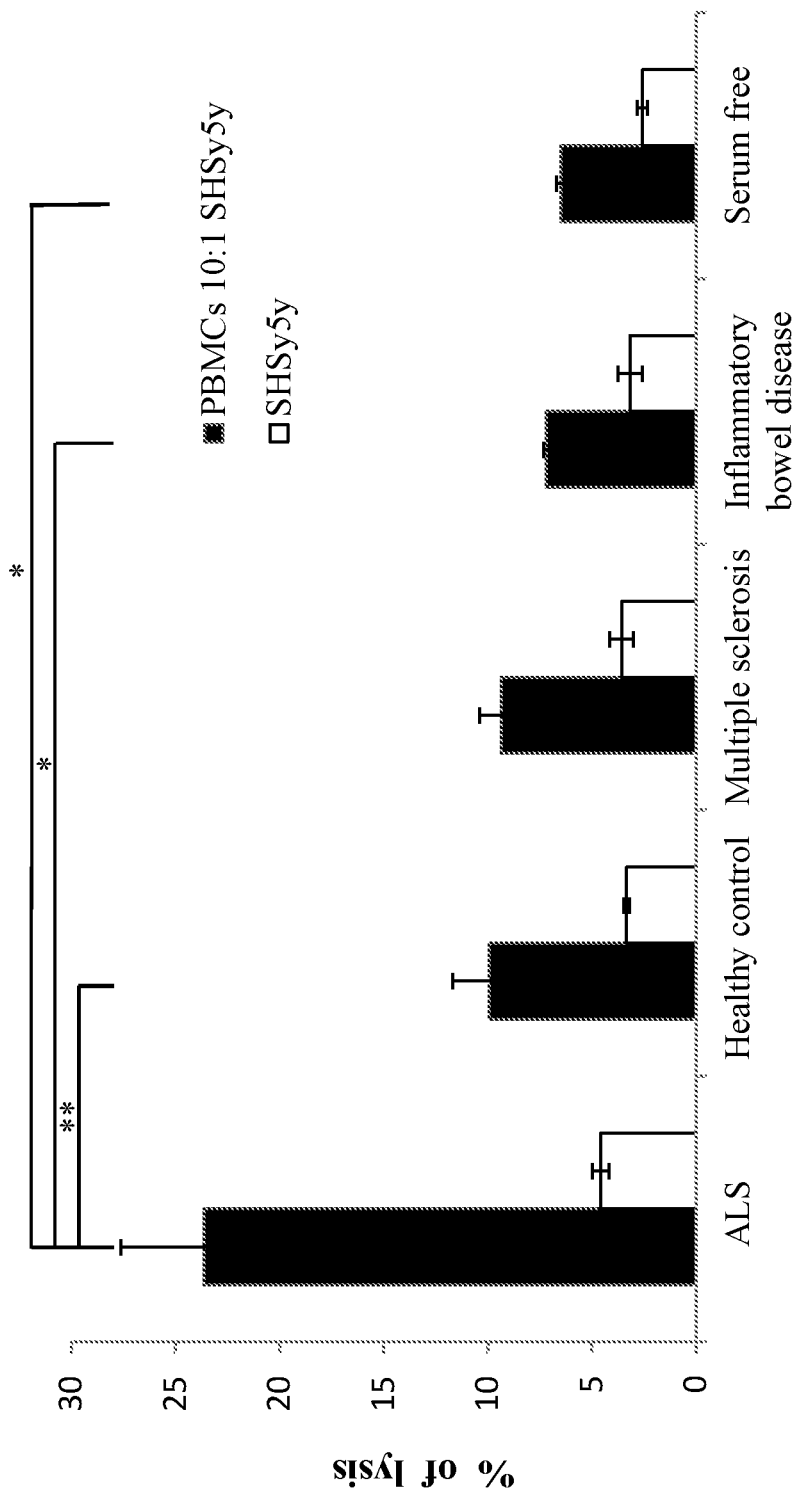
FIG. 14A is a bar graph showing results of an ADCC assay that was performed using human neuroblastoma as target cells, PBMCs as effector cells, and pools of serum samples of ALS, healthy control, inflammatory bowel disease patients, and multiple sclerosis patients as IgG sources. The controls contain: neuroblastoma cells incubated with IgG pools from the different serum sources and co-cultures of neuroblastoma cells and PBMCs.

Cytotoxic assays were performed using human neuroblastoma or mouse NSC34 as target cells to evaluate the involvement of ALS-derived IgG in mediating ADCC. PBMCs as effector cells and pools from healthy controls, ALS, inflammatory bowel disease, and multiple sclerosis patients were used as IgG sources. A lysis rate of 25% was mediated by IgG from ALS patient sera (FIG. 14A), while healthy control, inflammatory bowel disease patient and multiple sclerosis patient sera mediated cytotoxicity of less than 10% (FIG. 14A). A lysis rate of 7% was measured in samples of neuroblastoma cells co-cultured with PBMCs and values of less than 5% when neuroblastoma cells were incubated with IgG samples to control for spontaneous cell lysis.

Figure 14B:
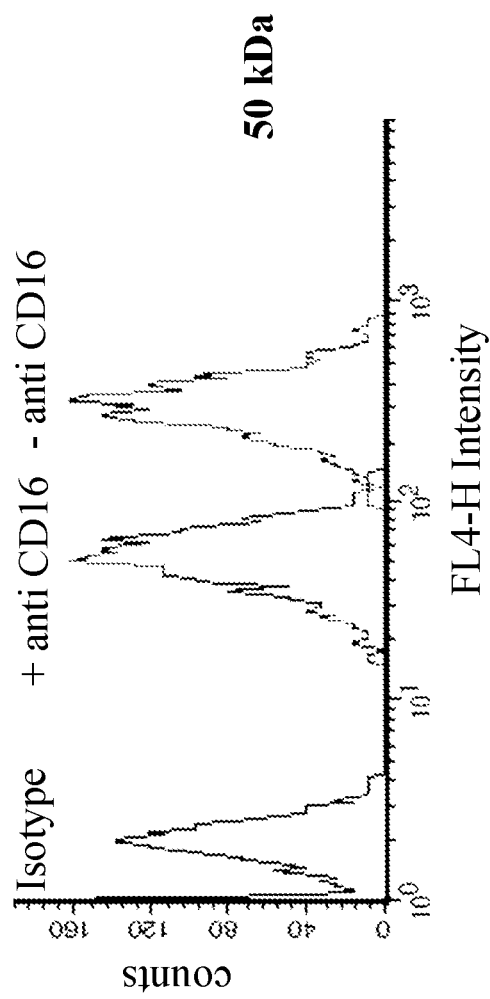
FIG. 14B is a FACS histogram showing results from PBMCs pre-treated with anti-CD16 antibodies.
Figure 14C:
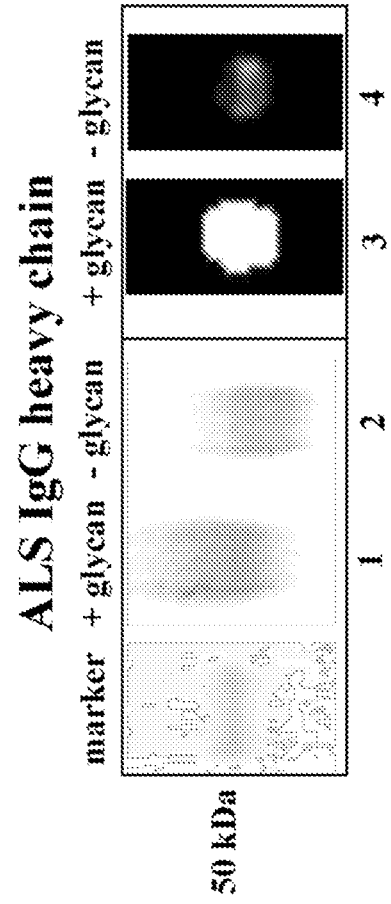
FIG. 14C are pictures SDS-PAGE and Western blot using ECL lectin of the heavy chain of ALS-IgG before and after PNGase-F treatment.
Figures 14D, 14E:
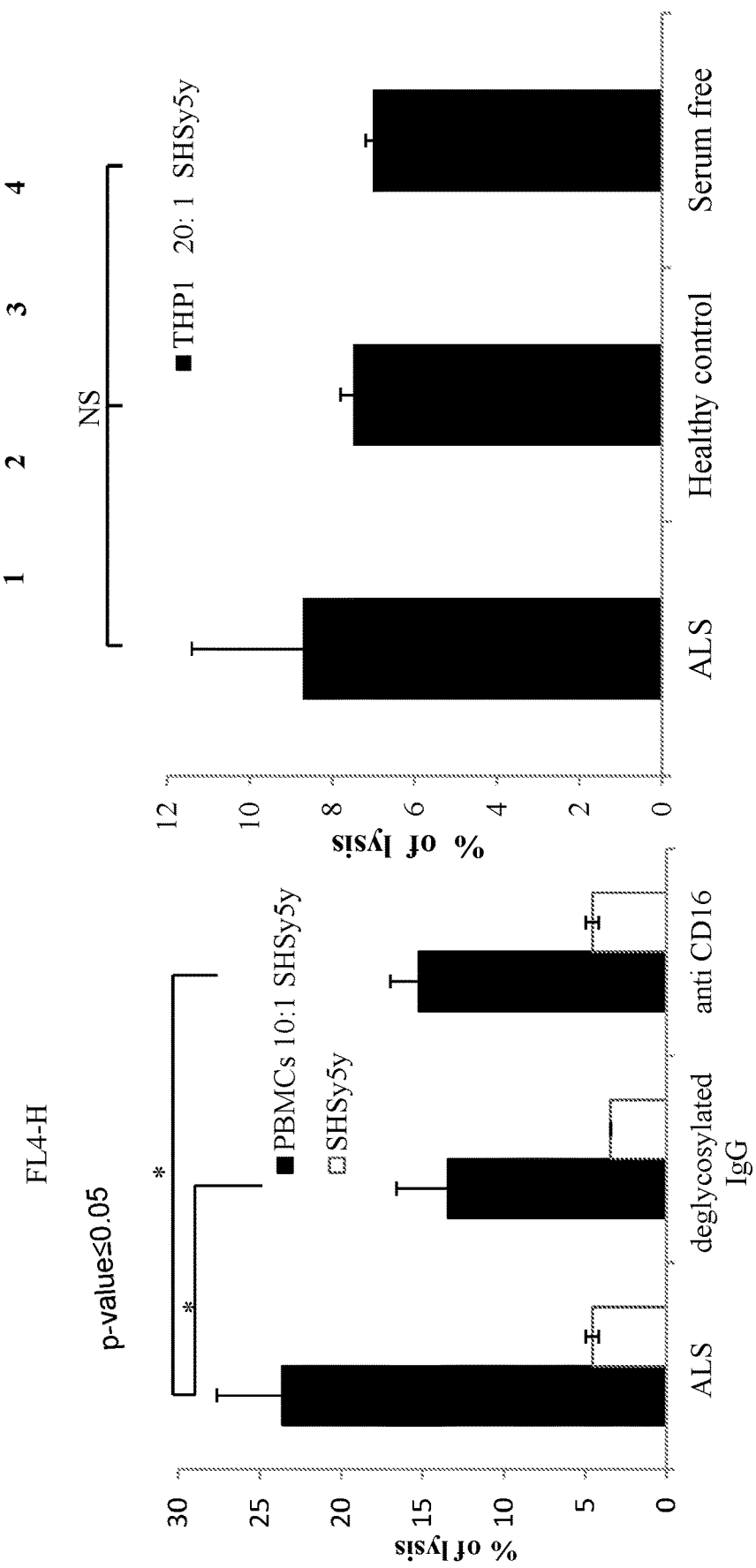
FIG. 14D is a bar graph showing killing of NSC34 cells by ADCC as described above was mediated by intact (untreated) ALS-IgG, PNGase-F treated ALS-IgG and by IgG from healthy controls.
FIG. 14E is a bar graph showing neuroblastoma lysis by CD32- and CD64-positive THP1 cells was mediated by ALS-IgG, IgG of healthy controls, and in serum free of IgG. * Spontaneous lysis was measured in neuroblastoma or NSC34 cultures. Triple staining of NeuN, Iba1, and ALS-IgG by anti-human IgGs conjugated to FITC demonstrates the localization of intact ALS-IgG in immune synapse (arrow) amongst microglia and neurons.

PBMCs were blocked with anti-CD16 antibodies and IgG were purified from pool samples to evaluate the involvement of CD16 in the ADCC reaction mediated by ALS-IgG. FACS results show a significant decrease in coupling of ALS-IgG to PBMCs, as detected by secondary antibodies (FIG. 14B left panel). Using the CD16-blocked PBMCs in an ADCC reaction against neuroblastoma cells led to a 40% reduction in the cytotoxic response against the target cells, in comparison to cell lysis with unblocked PBMCs (FIG. 14C). To illustrate the effect of the A2BG2 glycoform on neuroblastoma lysis, N-glycans were removed from ALS-IgG by PNGase F treatment and the heavy chain was assessed by SDS-PAGE and Western blot using ECL lectin conjugated to FITC. N-glycans with galactose residues have high affinity to the ECL lectin. As can be seen, the heavy chain of ALS-IgG before PNGase F treatment migrated with an average apparent molecular weight of 50 kDa (lane 1) and was well labeled in the Western blot protocol (lane 3) (FIG. 14B right). After PNGase F treatment, however, the heavy chain band was shifted to an apparent molecular weight lower than 50 kDa (lane 2), with the fluorescent intensity associated with the immunoblot being quenched (lane 4) (FIG. 14B right). When using ALS-IgG after PNGase F treatment in an ADCC response against neuroblastoma cells, a two-fold decrease in lysis was noted compared to using ALS-IgG bearing N-glycans (FIG. 14C). In comparable experiments, killing of NSC34 target cells by PBMCs was conducted using intact ALS-IgG, ALS-IgG treated with PNGase F and IgG from healthy control samples. A similar killing pattern of NSC34 cells as measured for neuroblastoma cells was mediated by intact ALS-IgG, the treated IgG and those from healthy controls (FIG. 14D). Furthermore, opsonizing of ALS-IgG by CD64 and CD32, which either leads to target cell lysis was reversed by using THP1 cells expressing CD32 and CD64 but not CD16, as an alternative to NK cells in the cytotoxic assay (FIG. 14E). These observations indicate that CD16 on NK cells and the A2BG2 in ALS-IgG are involved in neuroblastoma and NSC34 cell loss.

The localization of intact IgG derived from ALS patients with both neuron and microglia of mSOD1 brain tissue, by triple staining was analyzed to assess the feasibility of in vivo ADCC. Several ALS-IgG molecules were found to be located in the immune synapse between microglia and the neuron, suggesting the occurrence of ADCC (FIG. 14F). In contrast, such localization was rarely observed in matched-sections when PNGase-F-treated ALS-IgG were used (data not shown). Accordingly, the Fc glycans are involved in IgG deposition in the brain of an ALS animal model and plausibly take part in in vivo ADCC.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for increasing or enhancing phagocytic activity of microglia in a subject in need thereof, comprising administering to said subject a therapeutically effective amount of an immunoglobulin Fc fragment comprising the amino acid sequence as set forth in any one of SEQ ID NO: 1 and SEQ ID NO: 2, wherein said Fc fragment comprises the amino acid sequence as set forth in SEQ ID NO: 9, thereby increasing or enhancing phagocytic activity of microglia in said subject.

2. The method of claim 1, wherein said immunoglobulin Fc fragment has an increased affinity to an Fc receptor compared to a WT Fc fragment.

3. The method of claim 1, wherein said Fc receptor is CD16.

4. The method of claim 1, wherein said Fc receptor is expressed on a microglia cell.

5. The method of claim 1, wherein said immunoglobulin Fc fragment is an antagonist of CD16.

6. The method of claim 1, wherein said immunoglobulin Fc fragment comprises two polypeptides, each polypeptide comprising the amino acid sequence as set forth in SEQ ID NO: 9.

7. The method of claim 1, wherein said immunoglobulin Fc fragment comprises N297-glycan.

8. The method of claim 1, wherein said immunoglobulin Fc fragment comprises a bisecting N-acetyl glucosamine (GlcNAc).

* * * * *